(12) United States Patent
Carter et al.

(10) Patent No.: US 8,618,101 B2
(45) Date of Patent: Dec. 31, 2013

(54) N-((1R,2S,5R)-5-(TERT-BUTYLAMINO)-2-((S)-3-(7-TERT-BUTYLPYRAZOLO[1,5-A][1,3,5]TRIAZIN-4-YLAMINO)-2-OXOPYRROLIDIN-1-YL)CYCLOHEXYL)ACETAMIDE, A DUAL MODULATOR OF CHEMOKINE RECEPTOR ACTIVITY, CRYSTALLINE FORMS AND PROCESSES

(71) Applicant: Bristol-Myers Squibb Company, Princeton, NJ (US)

(72) Inventors: Percy H. Carter, Princeton, NJ (US); Robert J. Cherney, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/746,389

(22) Filed: Jan. 22, 2013

(65) Prior Publication Data

US 2013/0158039 A1    Jun. 20, 2013

Related U.S. Application Data

(63) Continuation of application No. 12/901,614, filed on Oct. 11, 2010, now Pat. No. 8,383,812.

(60) Provisional application No. 61/250,978, filed on Oct. 13, 2009.

(51) Int. Cl.
| C07D 487/04 | (2006.01) |
| A61K 31/53 | (2006.01) |
| A61P 19/02 | (2006.01) |
| A61P 35/00 | (2006.01) |

(52) U.S. Cl.
USPC ..................... 514/246; 544/194; 544/219

(58) Field of Classification Search
USPC .................. 514/246; 544/194, 219
See application file for complete search history.

(56) References Cited

U.S. PATENT DOCUMENTS

| 6,706,712 B2 | 3/2004 | Cherney |
| 6,974,836 B2 | 12/2005 | Carter et al. |
| 7,087,604 B2 | 8/2006 | Cherney |
| 7,157,470 B2 | 1/2007 | Smallheer et al. |
| 7,163,937 B2 | 1/2007 | Carter et al. |
| 7,183,270 B2 | 2/2007 | Cherney et al. |
| 7,230,133 B2 | 6/2007 | Carter |
| 7,291,615 B2 | 11/2007 | Cherney |
| 7,317,019 B2 | 1/2008 | Carter |
| 7,338,975 B2 | 3/2008 | Carter et al. |
| 7,378,409 B2 | 5/2008 | Carter et al. |
| 7,482,335 B2 | 1/2009 | Carter et al. |
| 7,629,351 B2 | 12/2009 | Carter et al. |
| 7,671,062 B2 | 3/2010 | Yang et al. |
| 8,383,812 B2 * | 2/2013 | Carter et al. .................. 544/194 |
| 2003/0171218 A1 | 9/2003 | Bojack et al. |
| 2004/0186143 A1 | 9/2004 | Carter et al. |
| 2004/0235836 A1 | 11/2004 | Cherney |
| 2005/0043392 A1 | 2/2005 | Carter |
| 2006/0069123 A1 | 3/2006 | Xia et al. |
| 2008/0027084 A1 | 1/2008 | Duncia et al. |

FOREIGN PATENT DOCUMENTS

| DE | 812 551 | 9/1951 |
| EP | 0 550 924 | 7/1993 |
| JP | 63-83082 | 4/1988 |

(Continued)

OTHER PUBLICATIONS

Abbadie, C. et al., "Impaired neuropathic pain responses in mice lacking the chemokine receptor CCR2", Proceedings of the National Academy of Sciences, vol. 100, No. 13, pp. 7947-7952 (2003).

(Continued)

Primary Examiner — Venkataraman Balasubramanian
(74) Attorney, Agent, or Firm — Terence J. Bogie

(57) ABSTRACT

The present invention provides a novel antagonist: N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide:

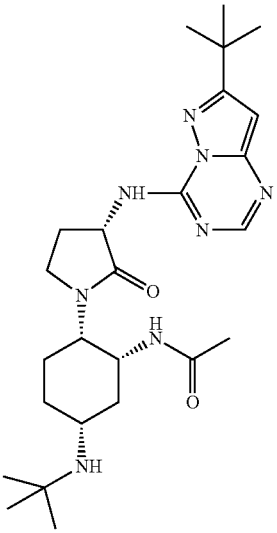

or a pharmaceutically acceptable salt, solvate or prodrug, thereof, having unexpected dual CCR-2 and CCR-5 receptor activity. Crystalline forms, metabolites, pharmaceutical compositions containing the same and methods of using the same as agents for the treatment of inflammatory diseases, allergic, autoimmune, metabolic, cancer and/or cardiovascular diseases are also disclosed. The present disclosure also provides processes for preparing compounds of Formula (I) as provided herein, including N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide. Compounds that are useful intermediates of the process are also provided herein.

2 Claims, 3 Drawing Sheets

(56) References Cited

FOREIGN PATENT DOCUMENTS

| WO | WO 97/05111 | 2/1997 |
|---|---|---|
| WO | WO 97/43257 | 11/1997 |
| WO | WO 98/01426 | 1/1998 |
| WO | WO 99/00362 | 1/1999 |
| WO | WO 99/07678 | 2/1999 |
| WO | WO 99/37304 | 7/1999 |
| WO | WO 99/38844 | 8/1999 |
| WO | WO 99/40914 | 8/1999 |
| WO | WO 99/46991 | 9/1999 |
| WO | WO 01/10799 | 2/2001 |
| WO | WO 01/17992 | 3/2001 |
| WO | WO 01/74783 | 10/2001 |
| WO | WO 01/74784 | 10/2001 |
| WO | WO 02/04416 | 1/2002 |
| WO | WO 02/50079 | 6/2002 |
| WO | WO 02/060859 | 8/2002 |
| WO | WO 02/078679 | 10/2002 |
| WO | WO 02/102372 | 12/2002 |
| WO | WO 03/005824 | 1/2003 |
| WO | WO 03/075853 | 9/2003 |
| WO | WO 2004/022536 | 3/2004 |
| WO | WO 2004/071460 | 8/2004 |
| WO | WO 2004/098516 | 11/2004 |
| WO | WO 2004/110376 | 12/2004 |
| WO | WO 2005/021500 | 3/2005 |
| WO | WO 2006/013427 | 2/2006 |
| WO | WO 2008/014360 | 1/2008 |
| WO | WO 2008/014361 | 1/2008 |
| WO | WO 2008/014381 | 1/2008 |

OTHER PUBLICATIONS

Abdi, R. et al., "Differential Role of CCR2 in Islet and Heart Allograft Rejection: Tissue Specificity of Chemokine/Chemokine Receptor Function In Vivo", The Journal of Immunology, vol. 172, pp. 767-775 (2004).
Andres, P.G. et al., "Mice with a Selective Deletion of the CC Chemokine Receptors 5 or 2 are Protected from Dextran Sodium Sulfate-Mediated Colitis: Lack of CC Chemokine Receptor 5 Expression Results in a NK1.1+ Lymphocyte-Associated Th2-Type Immune Response in the Intestine", The Journal of Immunology, vol. 164, pp. 6303-6312 (2000).
Antoniades, H.N. et al., "Expression of monocyte chemoattractant protein 1 mRNA in human idiopathic pulmonary fibrosis", Proc. Natl. Acad. Sci. USA, vol. 89, pp. 5371-5375 (1992).
Baba, M. et al., "Identification of CCR6, the Specific Receptor for a Novel Lymphocyte-directed CC Chemokine LARC", The Journal of Biological Chemistry, vol. 272, No. 23, pp. 14893-14898 (1997).
Belperio, J.A. et al., "Critical role for the chemokine MCP-1/CCR2 in the pathogenesis of bronchiolitis obliterans syndrome", The Journal of Clinical Investigation, vol. 108, No. 4, pp. 547-556 (2001).
Berman, J.W. et al., "Localization of Monocyte Chemoattractant Peptide-1 Expression in the Central Nervous System in Experimental Autoimmune Encephalomyelitis and Trauma in the Rat", The Journal of Immunology, vol. 156, pp. 3017-3023 (1996).
Bonini, J.A. et al., "Cloning, Expression, and Chromosomal Mapping of a Novel Human CC-Chemokine Receptor (CCR10) that Displays High-Affinity Binding for MCP-1 and MCP-3", DNA and Cell Biology, vol. 16, No. 10, pp. 1249-1256 (1997).
Boring, L. et al., "Decreased lesion formation in CCR2$^{-/-}$ mice reveals a role for chemokines in the initiation of atherosclerosis", Nature, vol. 394, pp. 894-897 (1998).
Boring, L. et al., "Impaired Monocyte Migration and Reduced Type 1 (Th1) Cytokine Responses in C-C Chemokine Receptor 2 Knockout Mice", The Journal of Clinical Investigation, vol. 100, No. 10, pp. 2552-2561 (1997).
Brodmerkel, C.M. et al., "Discovery and Pharmacological Characterization of a Novel Rodent-Active CCR2 Antagonist, INCB3344", The Journal of Immunology, vol. 175, pp. 5370-5378 (2005).
Brühl, H. et al., "Dual Role of CCR2 during Initiation and Progression of Collagen-Induced Arthritis: Evidence for Regulatory Activity of CCR2+ T Cells", The Journal of Immunology, vol. 172, pp. 890-898 (2004).
Bruun, J.M. et al., "Monocyte Chemoattractant Protein-1 Release is Higher in Visceral than Subcutaneous Human Adipose Tissue (AT): Implication of Macrophages Resident in the AT", The Journal of Clinical Endocrinology & Metabolism, vol. 90, No. 4, pp. 2282-2289 (2005).
Bush, E. et al., "CC Chemokine Receptor 2 is Required for Macrophage Infiltration and Vascular Hypertrophy in Angiotensin II-Induced Hypertension", Hypertension, vol. 36, pp. 360-363 (2000).
Carter, P.H., "Chemokine receptor antagonism as an approach to anti-inflammatory therapy: 'just right' or plain wrong?", Current Opinion in Chemical Biology, vol. 6, pp. 510-525 (2002).
Charo, I.F. et al., "Molecular cloning and functional expression of two monocyte chemoattractant protein 1 receptors reveals alternative splicing of the carboxyl-terminal tails", Proc. Natl. Acad. Sci. USA, vol. 91, pp. 2752-2756 (1994).
Charo, I.F. et al., "The Many Roles of Chemokines and Chemokine Receptors in Inflammation", The New England Journal of Medicine, vol. 354, No. 6, pp. 610-621 (2006).
Chen, A. et al., "Diet Induction of Monocyte Chemoattractant Protein-1 and its Impact on Obesity", Obesity Research, vol. 13, No. 8, pp. 1311-1320 (2005).
Chen, H., "Cellular inflammatory responses: Novel insights for obesity and insulin resistance", Pharmacological Research, vol. 53, pp. 469-477 (2006).
Chow, F.Y. et al., "Monocyte chemoattractant protein-1-induced tissue inflammation is critical for the development of renal injury but not type 2 diabetes in obese *db/db* mice", Diabetologia, vol. 50, pp. 471-480 (2007).
Cipollone, F. et al., "Elevated Circulating Levels of Monocyte Chemoattractant Protein-1 in Patients with Restenosis After Coronary Angioplasty", Arterioscler. Thromb. Vasc. Biol., vol. 21, pp. 327-334 (2001).
Combadiere, C. et al., "Cloning and Functional Expression of a Human Eosinophil CC Chemokine Receptor", The Journal of Biological Chemistry, vol. 270, No. 27, pp. 16491-16494 (1995).
Connor, R.I. et al., "Change in Coreceptor Use Correlates with Disease Progression in HIV-1-Infected Individuals", J. Exp. Med., vol. 185, No. 4, pp. 621-628 (1997).
Connor, S.J. et al., "CCR2 expressing CD4+ lymphocytes are preferentially recruited to the ileum in Crohn's disease", Gut, vol. 53, pp. 1287-1294 (2004).
Conti, I. et al., "CCL2 (monocyte chemoattractant protein-1) and cancer", Seminars in Cancer Biology, vol. 14, pp. 149-154 (2004).
Costain, W.J. et al., "Modulatory effects of PLG and its peptidomimetics on haloperidol-induced catalepsy in rats", Peptides, vol. 20, pp. 761-767 (1999).
Craig, M.J. et al., "CCL2 (Monocyte Chemoattractant Protein-1) in cancer bone metastases", Cancer Metastasis Rev., vol. 25, pp. 611-619 (2006).
Dandona, P. et al., "A Rational Approach to Pathogenesis and Treatment of Type 2 Diabetes Mellitus, Insulin Resistance, Inflammation, and Atherosclerosis", The American Journal of Cardiology, vol. 90, No. 5A, pp. 27G-33G (2002).
Dawson, J. et al., "Targeting monocyte chemoattractant protein-1 signalling in disease", Expert Opin. Ther. Targets, vol. 7, No. 1, pp. 35-48 (2003).
Dawson, T.C. et al., "Absence of CC chemokine receptor-2 reduces atherosclerosis in apolipoprotein E-deficient mice", Atherosclerosis, vol. 143, pp. 205-211 (1999).
Deleuran, M. et al., "Localization of monocyte chemotactic and activating factor (MCAF/MCP-1) in psoriasis", Journal of Dermatological Science, vol. 13, pp. 228-236 (1996).
Dimitrijevic, O.B. et al., "Absence of the Chemokine Receptor CCR2 Protects Against Cerebral Ischemia/Reperfusion Injury in Mice", Stroke, vol. 38, pp. 1345-1353 (2007).
Doranz, B.J. et al., "A Dual-Tropic Primary HIV-1 Isolate that Uses Fusin and the β-Chemokine Receptors CKR-5, CKR-3, and CKR-2b as Fusion Cofactors", Cell, vol. 85, pp. 1149-1158 (1996).

(56) References Cited

OTHER PUBLICATIONS

Dresser, G.K. et al., "Pharmacokinetic-Pharmacodynamic Consequences and Clinical Relevance of Cytochrome P450 3A4 Inhibition", Clin. Pharmacokinet., vol. 38, No. 1, pp. 41-57 (2000).
Eckel, R.H. et al., "The metabolic syndrome", The Lancet, vol. 365, pp. 1415-1428 (2005).
Egashira, K. et al., "Importance of Monocyte Chemoattractant Protein-1 Pathway in Neointimal Hyperplasia After Periarterial Injury in Mice and Monkeys", Circulation Research, vol. 90, pp. 1167-1172 (2002).
Evans, M.C. et al., "Synthesis and Dopamine Receptor Modulating Activity of Novel Peptidomimetics of L-Prolyl-L-leucyl-glycinamide Featuring α,α-Disubstituted Amino Acids", Journal of Medicinal Chemistry, vol. 42, No. 8, pp. 1441-1447 (1999).
Feria, M. et al., "The CCR2 receptor as a therapeutic target", Expert Opin. Ther. Patents, vol. 16, No. 1, pp. 49-57 (2006).
Ferreira, A.M. et al., "Diminished Induction of Skin Fibrosis in Mice with MCP-1 Deficiency", Journal of Investigative Dermatology, vol. 126, pp. 1900-1908 (2006).
Fife, B.T. et al., "CC Chemokine Receptor 2 is Critical for Induction of Experimental Autoimmune Encephalomyelitis", J. Exp. Med., vol. 192, No. 6, pp. 899-905 (2000).
Frangogiannis, N.G. et al., "Critical Role of Monocyte Chemoattractant Protein-1/CC Chemokine Ligand 2 in the Pathogenesis of Ischemic Cardiomyopathy", Circulation, vol. 115, pp. 584-592 (2007).
Gao, Z. et al., "Unraveling the Chemistry of Chemokine Receptor Ligands", Chemical Reviews, vol. 103, No. 9, pp. 3733-3752 (2003).
Gaupp, S. et al., "Experimental Autoimmune Encephalomyelitis (EAE) in CCR2$^{-/-}$ Mice", American Journal of Pathology, vol. 162, No. 1, pp. 139-150 (2003).
Gerhardt, C.C. et al., "Chemokines control fat accumulation and leptin secretion by cultured human adipocytes", Molecular and Cellular Endocrinology, vol. 175, pp. 81-92 (2001).
Gharaee-Kermani, M. et al., "CC-chemokine receptor 2 required for bleomycin-induced pulmonary fibrosis", Cytokine, vol. 24, pp. 266-276 (2003).
Giles, R. et al., "Can We Target the Chemokine Network for Cancer Therapeutics?", Current Cancer Drug Targets, vol. 6, No. 8, pp. 659-670 (2006).
Gillitzer, R. et al., "MCP-1 mRNA Expression in Basal Keratinocytes of Psoriatic Lesions", The Journal of Investigative Dermatology, vol. 101, No. 2, pp. 127-131 (1993).
Gong, J.-H. et al., "An Antagonist of Monocyte Chemoattractant Protein 1 (MCP-1) Inhibits Arthritis in the MRL-*lpr* Mouse Model", J. Exp. Med., vol. 186, No. 1, pp. 131-137 (1997).
Gonzalo, J.-A. et al., "The Coordinated Action of CC Chemokines in the Lung Orchestrates Allergic Inflammation and Airway Hyperresponsiveness", J. Exp. Med., vol. 188, No. 1, pp. 157-167 (1998).
Gosling, J. et al., "MCP-1 deficiency reduces susceptibility to atherosclerosis in mice that overexpress human apolipoprotein B", The Journal of Clinical Investigation, vol. 103, No. 6, pp. 773-778 (1999).
Grimm, M.C. et al., "Enhanced expression and production of monocyte chemoattractant protein-1 in inflammatory bowel disease mucosa", Journal of Leukocyte Biology, vol. 59, pp. 804-812 (1996).
Gu, L. et al., "Absence of Monocyte Chemoattractant Protein-1 Reduces Atherosclerosis in Low Density Lipoprotein Receptor-Deficient Mice", Molecular Cell, vol. 2, pp. 275-281 (1998).
Guo, J. et al., "Repopulation of Apolipoprotein E Knockout Mice with CCR2-Deficient Bone Marrow Progenitor Cells Does Not Inhibit Ongoing Atherosclerotic Lesion Development", Arterioscler. Thromb. Vasc. Biol., vol. 25, pp. 1014-1019 (2005).
Guo, J. et al., "Transplantation of Monocyte CC-Chemokine Receptor 2-Deficient Bone Marrow into ApoE3-Leiden Mice Inhibits Atherogenesis", Arterioscler. Thromb. Vasc. Biol., vol. 23, pp. 447-453 (2003).
Hasegawa, H. et al., "Antagonist of Monocyte Chemoattractant Protein 1 Ameliorates the Initiation and Progression of Lupus Nephritis and Renal Vasculitis in MRL/lpr Mice", Arthritis & Rheumatism, vol. 48, No. 9, pp. 2555-2566 (2003).
Hayashidani, S. et al., "Anti-Monocyte Chemoattractant Protein-1 Gene Therapy Attenuates Left Ventricular Remodeling and Failure After Experimental Myocardial Infarction", Circulation, vol. 108, pp. 2134-2140 (2003).
Horiguchi, K. et al., "Selective Chemokine and Receptor Gene Expressions in Allografts that Develop Transplant Vasculopathy", The Journal of Heart and Lung Transplantation, vol. 21, No. 10, pp. 1090-1100 (2002).
Horuk, R., "Molecular properties of the chemokine receptor family", Trends in Pharmacological Sciences, vol. 15, pp. 159-165 (1994).
Horvath, C. et al., "Targeting CCR2 or CD18 Inhibits Experimental In-Stent Restenosis in Primates: Inhibitory Potential Depends on Type of Injury and Leukocytes Targeted", Circulation Research, vol. 90, pp. 488-494 (2002).
Hughes, P.M. et al., "Monocyte Chemoattractant Protein-1 Deficiency is Protective in a Murine Stroke Model", Journal of Cerebral Blood Flow & Metabolism, vol. 22, No. 3, pp. 308-317 (2002).
Iarlori, C. et al., "Interferon β-1b modulates MCP-1 expression and production in relapsing-remitting multiple sclerosis", Journal of Neuroimmunology, vol. 123, pp. 170-179 (2002).
Ishibashi, M. et al., "Critical Role of Monocyte Chemoattractant Protein-1 Receptor CCR2 on Monocytes in Hypertension-Induced Vascular Inflammation and Remodeling", Circulation Research, vol. 94, pp. 1203-1210 (2004).
Izikson, L. et al., "Resistance to Experimental Autoimmune Encephalomyelitis in Mice Lacking the CC Chemokine Receptor (CCR)2", J. Exp. Med., vol. 192, No. 7, pp. 1075-1080 (2000).
Jones, M.L. et al., "Potential Role of Monocyte Chemoattractant Protein 1/JE in Monocyte/Macrophage-Dependent IgA Immune Complex Alveolitis in the Rat", The Journal of Immunology, vol. 149, No. 6, pp. 2147-2154 (1992).
Kamei, N. et al., "Overexpression of Monocyte Chemoattractant Protein-1 in Adipose Tissues Causes Macrophage Recruitment and Insulin Resistance", The Journal of Biological Chemistry, vol. 281, No. 36, pp. 26602-26614 (2006).
Kanda, H. et al., "MCP-1 contributes to macrophage infiltration into adipose tissue, insulin resistance, and hepatic steatosis in obesity", The Journal of Clinical Investigation, vol. 116, No. 6, pp. 1494-1505 (2006).
Karrer, S. et al., "The −2518 Promotor Polymorphism in the MCP-1 Gene is Associated with Systemic Sclerosis", The Journal of Investigative Dermatology, vol. 124, vol. 1, pp. 92-98 (2005).
Kennedy, K.J. et al., "Acute and relapsing experimental autoimmune encephalomyelitis are regulated by differential expression of the CC chemokines macrophage inflammatory protein-1α and monocyte chemotactic protein-1", Journal of Neuroimmunology, vol. 92, pp. 98-108 (1998).
Khan, W.I. et al., "Critical role of MCP-1 in the pathogenesis of experimental colitis in the context of immune and enterochromaffin cells", Am. J. Physiol. Gastrointest. Liver Physiol., vol. 291, pp. G803-G811 (2006).
Kim, J.S. et al., "Expression of monocyte chemoattractant protein-1 and macrophage inflammatory protein-1 after focal cerebral ischemia in the rat", Journal of Neuroimmunology, vol. 56, pp. 127-134 (1995).
Kim, W.J.H. et al., "MCP-1 deficiency is associated with reduced intimal hyperplasia after arterial injury", Biochemical and Biophysical Research Communications, vol. 310, pp. 936-942 (2003).
Kitagawa, K. et al., "Blockade of CCR2 Ameliorates Progressive Fibrosis in Kidney", American Journal of Pathology, vol. 165, No. 1, pp. 237-246 (2004).
Koch, A.E. et al., "Enhanced Production of Monocyte Chemoattractant Protein-1 in Rheumatoid Arthritis", The Journal of Clinical Investigation, vol. 90, pp. 772-779 (1992).
Kurihara, T. et al., "Defects in Macrophage Recruitment and Host Defense in Mice Lacking the CCR2 Chemokine Receptor", J. Exp. Med., vol. 186, No. 10, pp. 1757-1762 (1997).
Kuziel, W.A. et al., "Severe reduction in leukocyte adhesion and monocyte extravasation in mice deficient in CC chemokine receptor 2", Proc. Natl. Acad. Sci. USA, vol. 94, pp. 12053-12058 (1997).
Lee, I. et al., "Blocking the Monocyte Chemoattractant Protein-1/CCR2 Chemokine Pathway Induces Permanent Survival of Islet

(56) References Cited

OTHER PUBLICATIONS

Allografts through a Programmed Death-1 Ligand-1-Dependent Mechanism", The Journal of Immunology, vol. 171, pp. 6929-6935 (2003).

Liu, T. et al., "Depletion of macrophages reduces axonal degeneration and hyperalgesia following nerve injury", Pain, vol. 86, pp. 25-32 (2000).

Lloyd, C.M. et al., "RANTES and Monocyte Chemoattractant Protein-1 (MCP-1) Play an Important Role in the Inflammatory Phase of Crescentic Nephritis, but Only MCP-1 is Involved in Crescent Formation and Interstitial Fibrosis", J. Exp. Med., vol. 185, No. 7, pp. 1371-1380 (1997).

Lu, B. et al., "Abnormalities in Monocyte Recruitment and Cytokine Expression in Monocyte Chemoattractant Protein 1-deficient Mice", J. Exp. Med., vol. 187, No. 4, pp. 601-608 (1998).

Lu, Y. et al., "CCR2 Expression Correlates with Prostate Cancer Progression", Journal of Cellular Biochemistry, vol. 101, pp. 676-685 (2007).

Lu, Y. et al., "Monocyte Chemotactic Protein-1 (MCP-1) Acts as a Paracrine and Autocrine Factor for Prostate Cancer Growth and invasion", The Prostate, vol. 66, pp. 1311-1318 (2006).

Lu, Y. et al., "Monocyte Chemotactic Protein-1 Mediates Prostate Cancer-Induced Bone Resorption", Cancer Research, vol. 67, No. 8, pp. 3646-3653 (2007).

Lukacs, N.W. et al., "Differential Recruitment of Leukocyte Populations and Alteration of Airway Hyperreactivity by C-C Family Chemokines in Allergic Airway Inflammation", The Journal of Immunology, vol. 158, pp. 4398-4404 (1997).

Lumeng, C.N. et al., "Increased Inflammatory Properties of Adipose Tissue Macrophages Recruited During Diet-Induced Obesity", Diabetes, vol. 56, pp. 16-23 (2007).

Lumeng, C.N. et al., "Obesity induces a phenotypic switch in adipose tissue macrophage polarization", The Journal of Clinical Investigation, vol. 117, No. 1, pp. 175-184 (2007).

Luster, A.D., "Chemokines—Chemotactic Cytokines that Mediate Inflammation", The New England Journal of Medicine, vol. 338, No. 7, pp. 436-445 (1998).

Napolitano, M. et al., "Molecular Cloning of *TER1*, a Chemokine Receptor-Like Gene Expressed by Lymphoid Tissues", The Journal of Immunology, vol. 157, pp. 2759-2763 (1996).

Neels, J.G. et al., "Inflamed fat: what starts the fire?", The Journal of Clinical Investigation, vol. 116, No. 1, pp. 33-35 (2006).

Neote, K. et al., "Molecular Cloning, Functional Expression, and Signaling Characteristics of a C-C Chemokine Receptor", Cell, vol. 72, pp. 415-425 (1993).

Ni, W. et al., "New Anti-Monocyte Chemoattractant Protein-1 Gene Therapy Attenuates Atherosclerosis in Apolipoprotein E-Knockout Mice", Circulation, vol. 103, pp. 2096-2101 (2001).

Nomura, S. et al., "Significance of chemokines and activated platelets in patients with diabetes", Clinical and Experimental Immunology, vol. 121, pp. 437-443 (2000).

Ogata, H. et al., "The Role of Monocyte Chemoattractant Protein-1 (MCP-1) in the Pathogenesis of Collagen-Induced Arthritis in Rats", Journal of Pathology, vol. 182, pp. 106-114 (1997).

Okuma, T. et al., "C-C chemokine receptor 2 (CCR2) deficiency improves bleomycin-induced pulmonary fibrosis by attenuation of both macrophage infiltration and production of macrophage-derived matrix metalloproteinases", Journal of Pathology, vol. 204, pp. 594-604 (2004).

Pérez de Lema, G. et al., "Chemokine Receptor Ccr2 Deficiency Reduces Renal Disease and Prolongs Survival in MRL/lpr Lupus-Prone Mice", Journal of the American Society of Nephrology, vol. 16, pp. 3592-3601 (2005).

Pickup, J.C. et al., "Is Type II diabetes mellitus a disease of the innate immune system?", Diabetologia, vol. 41, pp. 1241-1248 (1998).

Power, C.A. et al., "Molecular Cloning and Functional Expression of a Novel CC Chemokine Receptor cDNA from a Human Basophilic Cell Line", The Journal of Biological Chemistry, vol. 270, No. 33, pp. 19495-19500 (1995).

Premack, B.A. et al., "Chemokine receptors: Gateways to inflammation and infection", Nature Medicine, vol. 2, No. 11, pp. 1174-1178 (1996).

Quinones, M.P. et al., "CC chemokine receptor (CCR)-2 prevents arthritis development following infection by *Mycobacterium avium*", J. Mol. Med., vol. 84, pp. 503-512 (2006).

Quinones, M.P. et al., "Experimental arthritis in CC chemokine receptor 2-null mice closely mimics severe human rheumatoid arthritis", The Journal of Clinical Investigation, vol. 113, No. 6, pp. 856-866 (2004).

Reinecker, H.-C. et al., "Monocyte-Chemoattractant Protein 1 Gene Expression in Intestinal Epithelial Cells and Inflammatory Bowel Disease Mucosa", Gastroenterology, vol. 108, No. 1, pp. 40-50 (1995).

Reynaud-Gaubert, M. et al., "Upregulation of Chemokines in Bronchoalveolar Lavage Fluid as a Predictive Marker of Post-Transplant Airway Obliteration", The Journal of Heart and Lung Transplantation, vol. 21, No. 7, pp. 721-730 (2002).

Rezaie-Majd, A. et al., "Simvastatin Reduces Expression of Cytokines Interleukin-6, Interleukin-8, and Monocyte Chemoattractant Protein-1 in Circulating Monocytes from Hypercholesterolemic Patients", Arterioscler. Thromb. Vasc. Biol., vol. 22, pp. 1194-1199 (2002).

Rollins, B.J., "Chemokines", Blood, vol. 90, No. 3, pp. 909-928 (1997).

Roque, M. et al., "CCR2 Deficiency Decreases Intimal Hyperplasia After Arterial Injury", Arterioscler. Thromb. Vasc. Biol., vol. 22, pp. 554-559 (2002).

Russell, M.E. et al., "Early and persistent induction of monocyte chemoattractant protein 1 in rat cardiac allografts", Proc. Natl. Acad. Sci. USA, vol. 90, pp. 6086-6090 (1993).

Saiura, A. et al., "Antimonocyte Chemoattractant Protein-1 Gene Therapy Attenuates Graft Vasculopathy", Arterioscler. Thromb. Vasc. Biol., vol. 24, pp. 1886-1890 (2004).

Salcedo, R. et al., "Human endothelial cells express CCR2 and respond to MCP-1: direct role of MCP-1 in angiogenesis and tumor progression", Blood, vol. 96, No. 1, pp. 34-40 (2000).

Samad, F. et al., "Tumor necrosis factor α is a key component in the obesity-linked elevation of plasminogen activator inhibitor 1", Proc. Natl. Acad. Sci. USA, vol. 96, pp. 6902-6907 (1999).

Samson, M. et al., "Molecular Cloning and Functional Expression of a New Human CC-Chemokine Receptor Gene", Biochemistry, vol. 35, No. 11, pp. 3362-3367 (1996).

Sartipy, P. et al., "Monocyte chemoattractant protein 1 in obesity and insulin resistance", Proceedings of the National Academy of Sciences, vol. 100, No. 12, pp. 7265-7270 (2003).

Saunders, J. et al., "Opportunities for novel therapeutic agents acting at chemokine receptors", Drug Discovery Today, vol. 4, No. 2, pp. 80-92 (1999).

Schimmer, R.C. et al., "Streptococcal Cell Wall-Induced Arthritis: Requirements for IL-4, IL-10, IFN-γ, and Monocyte Chemoattractant Protein-1", The Journal of Immunology, vol. 160, pp. 1466-1471 (1998).

Schober, A. et al., "Crucial Role of the CCL2/CCR2 Axis in Neointimal Hyperplasia After Arterial Injury in Hyperlipidemic Mice Involves Early Monocyte Recruitment and CCL2 Presentation on Platelets", Circulation Research, vol. 95, pp. 1125-1133 and online data supplement (2004).

Schweickart, V.L. et al., "CCR11 is a Functional Receptor for the Monocyte Chemoattractant Protein Family of Chemokines", The Journal of Biological Chemistry, vol. 275, No. 13, pp. 9550-9556 (2000), and vol. 276, No. 1, p. 856 (2001) (errata sheet).

Shimizu, S. et al., "Anti-monocyte chemoattractant protein-1 gene therapy attenuates nephritis in MRL/lpr mice", Rheumatology, vol. 43, pp. 1121-1128 (2004).

Smith, M.W. et al., "Contrasting Genetic Influence of *CCR2* and *CCR5* Variants on HIV-1 Infection and Disease Progression", Science, vol. 277, pp. 959-965 (1997).

Spagnolo, P. et al., "C-C Chemokine Receptor 2 and Sarcoidosis: Association with Löfgren's Syndrome", American Journal of Respiratory and Critical Care Medicine, vol. 168, pp. 1162-1166 (2003).

(56) References Cited

OTHER PUBLICATIONS

Tacke, F. et al., "Monocyte subsets differentially employ CCR2, CCR5, and CX3CR1 to accumulate within atherosclerotic plaques", The Journal of Clinical Investigation, vol. 117, No. 1, pp. 185-194 (2007).

Tatewaki, H. et al., "Blockade of monocyte chemoattractant protein-1 by adenoviral gene transfer inhibits experimental vein graft neointimal formation", Journal of Vascular Surgery, vol. 45, No. 6, pp. 1236-1243 (2007).

Tesch, G.H. et al., "Monocyte Chemoattractant Protein 1-dependent Leukocyte Infiltrates are Responsible for Autoimmune Disease in MRL-$Fas^{lpr}$ Mice", J. Exp. Med., vol. 190, No. 12, pp. 1813-1824 (1999).

Tesch, G.H. et al., "Monocyte chemoattractant protein-1 promotes macrophage-mediated tubular injury, but not glomerular injury, in nephrotoxic serum nephritis", The Journal of Clinical Investigation, vol. 103, No. 1, pp. 73-80 (1999).

Tokuyama, H. et al., "The simultaneous blockade of chemokine receptors CCR2, CCR5 and CXCR3 by a non-peptide chemokine receptor antagonist protects mice from dextran sodium sulfate-mediated colitis", International Immunology, vol. 17, No. 8, pp. 1023-1034 (2005).

Trivedi, B.K. et al., Chapter 17: "Chemokines: Targets for Novel Therapeutics", Annual Reports in Medicinal Chemistry, vol. 35, Academic Press, publ., pp. 191-200 (2000).

Tsou, C.-L. et al., "Critical roles for CCR2 and MCP-3 in monocyte mobilization from bone marrow and recruitment to inflammatory sites", The Journal of Clinical Investigation, vol. 117, No. 4, pp. 902-909 (2007).

Tsuruta, S. et al., "Anti-monocyte chemoattractant protein-1 gene therapy prevents dimethylnitrosamine-induced hepatic fibrosis in rats", International Journal of Molecular Medicine, vol. 14, pp. 837-842 (2004).

Vestergaard, C. et al., "Expression of CCR2 on Monocytes and Macrophages in Chronically Inflamed Skin in Atopic Dermatitis and Psoriasis", Acta Derm. Venereol., vol. 84, pp. 353-358 (2004).

Wada, T. et al., "Gene Therapy via Blockade of Monocyte Chemoattractant Protein-1 for Renal Fibrosis", Journal of the American Society of Nephrology, vol. 15, pp. 940-948 (2004).

Walton, E. et al., "Search for New Analgesics. Part I. Homologues of Pethidine and Related Compounds", Journal of the Chemical Society, pp. 315-319 (1945).

Weisberg, S.P. et al., "CCR2 modulates inflammatory and metabolic effects of high-fat feeding", The Journal of Clinical Investigation, vol. 116, No. 1, pp. 115-124 (2006).

Weisberg, S.P. et al., "Obesity is associated with macrophage accumulation in adipose tissue", The Journal of Clinical Investigation, vol. 112, No. 12, pp. 1796-1808 (2003).

Wells, T.N.C. et al., "Plagiarism of the host immune system: lessons about chemokine immunology from viruses", Current Opinion in Biotechnology, vol. 8, pp. 741-748 (1997).

Xu, H. et al., "Chronic inflammation in fat plays a crucial role in the development of obesity-related insulin resistance", The Journal of Clinical Investigation, vol. 112, No. 12, pp. 1821-1830 (2003).

Yamamoto, T. et al., "Role of Monocyte Chemoattractant Protein-1 and its Receptor, CCR-2, in the Pathogenesis of Bleomycin-Induced Scleroderma", The Journal of Investigative Dermatology, vol. 121, No. 3, pp. 510-516 (2003).

Yoshio, O. et al., "Novel lymphocyte-specific CC chemokines and their receptors", Journal of Leukocyte Biology, vol. 62, pp. 634-644 (1997).

Youssef, S. et al., "C—C chemokine-encoding DNA vaccines enhance breakdown of tolerance to their gene products and treat ongoing adjuvant arthritis", The Journal of Clinical Investigation, vol. 106, No. 3, pp. 361-371 (2000).

Zlotnik, A. et al., "Chemokines: A New Classification System and Their Role in Immunity", Immunity, vol. 12, pp. 127-127 (2000).

Cecil Textbook of Medicine, edited by Bennet, J.C., and Plum F., 2oth edition, vol. 1, pp. 1004-1010 (1996).

Dermer, et al., "Another Anniversary for the War on Cancer", Bio/Technology vol. 12, p. 320 (1994).

Freshney, et al., Culture of Animal Cells, A Manual of Basic Technique, Alan R. Liss, Inc. New York, p. 4 (1983).

Golub, T.R. et al., "Molecular Classification of Cancer: Class Discovery and Class Prediction by Gene Expression Monitoring", Science, vol. 286, pp. 531-537 (1999).

Raman, D. et al., "Role of chemokines in tumor growth", Cancer Letters, vol. 256, pp. 137-165 (2007).

\* cited by examiner

Experimental and simulated powder patterns of N-((1R,2S,5R)-5-(*tert*-butylamino)-2-((S)-3-(7-*tert*-butylpyrazolo[1,5-a][1,3,5]triazin-4-ylamino)-2-oxopyrrolidin-1-yl)cyclohexyl)acetamide (Example 5)

DSC of the N-((1R,2S,5R)-5-(*tert*-butylamino)-2-((S)-3-(7-*tert*-butylpyrazolo[1,5-a][1,3,5]triazin-4-ylamino)-2-oxopyrrolidin-1-yl)cyclohexyl)acetamide, free base Form N-1 (Example 5)

TGA of N-((1R,2S,5R)-5-(*tert*-butylamino)-2-((S)-3-(7-*tert*-butylpyrazolo[1,5-a][1,3,5]triazin-4-ylamino)-2-oxopyrrolidin-1-yl)cyclohexyl)acetamide free base Form N-1 (Example 5)

N-((1R,2S,5R)-5-(*TERT*-BUTYLAMINO)-2-((S)-3-(7-*TERT*-BUTYLPYRAZOLO[1,5-A][1,3,5]TRIAZIN-4-YLAMINO)-2-OXOPYRROLIDIN-1-YL)CYCLOHEXYL) ACETAMIDE, A DUAL MODULATOR OF CHEMOKINE RECEPTOR ACTIVITY, CRYSTALLINE FORMS AND PROCESSES

RELATED APPLICATIONS

This application is a continuation of U.S. application Ser. No. 12/901,614, filed Oct. 11, 2010, now U.S. Pat. No. 8,383,812, which claims the benefit of U.S. Provisional Application No. 61/250,978, filed Oct. 13, 2009, the contents of which are herein 10 incorporated by reference in their entirety.

FIELD OF THE INVENTION

The present invention provides N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, or a pharmaceutically acceptable salt, solvate or prodrug, thereof, having unexpected desirable dual activity. Crystalline forms of the present invention are also provided. Pharmaceutical compositions containing the same and methods of using the same as agents for the treatment of inflammatory diseases, allergic, autoimmune, metabolic, cancer and/or cardiovascular diseases is also an objective of this invention. The present disclosure also provides a process for preparing compounds of Formula (I), including N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide:

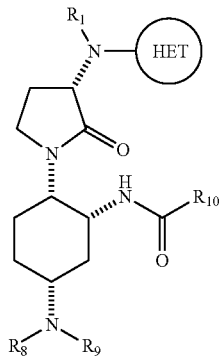

I wherein $R^1$, $R^8$, $R^9$, $R^{10}$, and

are as described herein. Compounds that are useful intermediates of the process are also provided herein. Metabolites of active compounds, pharmaceutical compositions, and use thereof are also provided herein.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in: Charo et al., *New Eng. J. Med.*, 354:610-621 (2006); Luster, *New Eng. J. Med.*, 338:436-445 (1998); and Rollins, *Blood,* 90:909-928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.,* 15:159-165 (1994)) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik et al., *Immunity,* 12:121 (2000)): CCR-1 (or "CKR-1" or "CC-CKR-1") [MIP-1α, MCP-3, MCP-4, RANTES] (Ben-Barruch et al., *Cell,* 72:415-425 (1993), and Luster, *New Eng. J. Med.,* 338:436-445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., *Proc. Natl. Acad. Sci. USA,* 91:2752-2756 (1994), and Luster, *New Eng. J. Med.,* 338:436-445 (1998)); CCR-3 (or "CKR-3" or "CC-CKR-3") [eotaxin-1, eotaxin-2, RANTES, MCP-3, MCP-4] (Combadiere et al., *J. Biol. Chem.,* 270:16491-16494 (1995), and Luster, *New Eng. J. Med.,* 338:436-445 (1998)); CCR-4 (or "CKR-4" or "CC-CKR-4") [TARC, MDC] (Power et al., *J. Biol. Chem.,* 270:19495-19500 (1995), and Luster, *New Eng. J. Med.,* 338:436-445 (1998)); CCR-5 (or "CKR-5" OR "CC-CKR-5") [MIP-1α, RANTES, MIP-1β] (Samson et al., *Biochemistry,* 35:3362-3367 (1996)); CCR-6 (or "CKR-6" or "CC-CKR-6") [LARC] (Baba et al., *J. Biol. Chem.,* 272:14893-14898 (1997)); CCR-7 (or "CKR-7" or "CC-CKR-7") [ELC] (Yoshie et al., *J. Leukoc. Biol.,* 62:634-644 (1997)); CCR-8 (or "CKR-8" or "CC-CKR-8") [I-309] (Napolitano et al., *J. Immunol.,* 157:2759-2763 (1996)); CCR-10 (or "CKR-10" or "CC-CKR-10") [MCP-1, MCP-3] (Bonini et al., *DNA Cell Biol.,* 16:1249-1256 (1997)); and CCR-11 [MCP-1, MCP-2, and MCP-4] (Schweickart et al., *J. Biol. Chem.,* 275:9550 (2000)).

In addition to the mammalian chemokine receptors, mammalian cytomegaloviruses, herpesviruses and poxviruses have been shown to express, in infected cells, proteins with the binding properties of chemokine receptors (reviewed in: Wells et al., *Curr. Opin. Biotech.,* 8:741-748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR-2, CCR-3, CCR-5 and CCR-8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases; as well as autoimmune pathologies, such as rheumatoid arthritis and multiple sclerosis; and metabolic diseases, such as atherosclerosis and diabetes (reviewed in: Charo et al., *New Eng. J. Med.*, 354:610-621 (2006); Gao, Z. et al., *Chem. Rev.*, 103:3733 (2003); Carter, P. H., *Curr. Opin. Chem. Biol.*, 6:510 (2002); Trivedi et al., *Ann. Reports Med. Chem.*, 35:191 (2000); Saunders et al., *Drug Disc. Today*, 4:80 (1999); Premack et al., *Nature Medicine*, 2:1174 (1996)). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, and the promotion of leukocyte migration. Demonstration of the importance of the MCP-1/CCR-2 interaction has been provided by experiments with genetically modified mice. MCP-1–/– mice were unable to recruit monocytes into sites of inflammation after several different types of immune challenge (Lu, B. et al., *J. Exp. Med.*, 187:601 (1998)). Likewise, CCR-2–/– mice were unable to recruit monocytes or produce interferon-γ when challenged with various exogenous agents; moreover, the leukocytes of CCR-2 null mice did not migrate in response to MCP-1 (Boring, L. et al., *J. Clin. Invest.*, 100:2552 (1997)), thereby demonstrating the specificity of the MCP-1/CCR-2 interaction. Two other groups have independently reported equivalent results with different strains of CCR-2–/– mice (Kuziel, W. A. et al., *Proc. Natl. Acad. Sci. USA*, 94:12053 (1997), and Kurihara, T. et al., *J. Exp. Med.*, 186:1757 (1997)). The viability and generally normal health of the MCP-1–/– and CCR-2–/– animals is noteworthy, in that disruption of the MCP-1/CCR-2 interaction does not induce physiological crisis. Taken together, these data lead one to the conclusion that molecules that block the actions of MCP-1/CCR-2 would be useful in treating a number of inflammatory and autoimmune disorders (reviewed in: Feria, M. et al., *Exp. Opin. Ther. Patents*, 16:49 (2006); and Dawson, J. et al., *Exp. Opin. Ther. Targets*, 7:35 (2003)). This hypothesis has now been validated in a number of different animal disease models, as described below.

It is known that MCP-1 is upregulated in patients with rheumatoid arthritis (Koch, A. et al., *J. Clin. Invest.*, 90:772-779 (1992)). Moreover, several preclinical studies have demonstrated the potential therapeutic value of antagonism of the MCP-1/CCR-2 interaction in treating rheumatoid arthritis. A DNA vaccine encoding MCP-1 was shown recently to ameliorate chronic polyadjuvant-induced arthritis in rats (Youssef, S. et al., *J. Clin. Invest.*, 106:361 (2000)). Likewise, the disease symptoms could be controlled via direct administration of antibodies for MCP-1 to rats with collagen-induced arthritis (Ogata, H. et al., *J. Pathol.*, 182:106 (1997)), or streptococcal cell wall-induced arthritis (Schimmer, R. C. et al., *J. Immunol.*, 160:1466 (1998)). Perhaps most significantly, a peptide antagonist of MCP-1, MCP-1 (9-76), was shown both to prevent disease onset and to reduce disease symptoms (depending on the time of administration) in the MRL-1pr mouse model of arthritis (Gong, J.-H. et al., *J. Exp. Med.*, 186:131 (1997)). Moreover, it has been demonstrated the administration of small molecule CCR-2 antagonists reduced clinical score in rodent models of arthritis (Brodmerkel, C. M. et al., *J. Immunol.*, 175:5370 (2005); and Xia, M. et al., U.S. Publication No. 2006/0069123). Administration of an anti-CCR-2 antibody had varying effects on murine CIA, depending on the time of administration (Bruhl, H. et al., *J. Immunol.*, 172:890 (2004)). Recent studies with CCR-2–/– mice have suggested that deletion of CCR-2 can exacerbate rodent arthritis models in specific experimental circumstances (Quinones, M. P. et al., *J. Clin. Invest.*, 113:856 (2004); Quinones, M. P. et al., *J. Mol. Med.*, 84:503 (2006)).

It is known that MCP-1 is upregulated in atherosclerotic lesions, and it has been shown that circulating levels of MCP-1 are reduced through treatment with therapeutic agents (Rezaie-Majd, A. et al., *Arterioscler. Thromb. Vasc. Biol.*, 22:1194-1199 (2002)). Several key studies have demonstrated the potential therapeutic value of antagonism of the MCP-1/CCR-2 interaction in treating atherosclerosis. For example, when MCP-1–/– mice are crossed with LDL receptor-deficient mice, an 83% reduction in aortic lipid deposition was observed (Gu, L. et al., *Mol. Cell*, 2:275 (1998)). Similarly, when MCP-1 was genetically ablated from mice which already overexpressed human apolipoprotein B, the resulting mice were protected from atherosclerotic lesion formation relative to the MCP-1+/+ apoB control mice (Gosling, J. et al., *J. Clin. Invest.*, 103:773 (1999)). Likewise, when CCR-2–/– mice are crossed with apolipoprotein E–/– mice, a significant decrease in the incidence of atherosclerotic lesions was observed (Boring, L. et al., *Nature*, 394:894 (1998); Dawson, T. C. et al., *Atherosclerosis*, 143:205 (1999)). Finally, when apolipoprotein E–/– mice are administered a gene encoding a peptide antagonist of CCR-2, then lesion size is decreased and plaque stability is increased (Ni, W. et al., *Circulation*, 103:2096-2101 (2001)). Transplantation of bone marrow from CCR-2–/– mice into ApoE3-Leiden mice inhibited early atherogenesis (Guo, J. et al., *Arterioscler. Thromb. Vasc. Biol.*, 23:447 (2003)), but had minimal effects on advanced lesions (Guo, J. et al., *Arterioscler. Thromb. Vasc. Biol.*, 25:1014 (2005)).

Patients with type 2 diabetes mellitus typically exhibit insulin resistance as one of the hallmark features of the disease. Insulin resistance is also associated with the grouping of abnormalities known as the "metabolic syndrome" or "syndrome X," which includes obesity, atherosclerosis, hypertension, and dyslipidemia (reviewed in: Eckel et al., *Lancet*, 365:1415 (2005)). It is well-recognized that inflammation plays a role in exacerbating the disease process in type 2 diabetes and the "syndrome X" pathologies (reviewed in: Chen, H., *Pharmacological Research*, 53:469 (2006); Neels et al., *J. Clin. Invest.*, 116:33 (2006); Danadona et al., *Am. J. Cardiol.*, 90:27 G-33G (2002); Pickup et al., *Diabetologia*, 41:1241 (1998)). MCP-1 is recognized as playing a role in obesity-induced insulin resistance. In culture, human preadipocytes constitutively expressed MCP-1 (Gerhardt, *Mol. Cell. Endocrinology*, 175:81 (2001)). CCR-2 is expressed on adipocytes; Addition of MCP-1 to differentiated adipocytes in vitro decreases insulin-stimulated glucose uptake and the expression of several adipogenic genes (LpL, adipsin, GLU-4), aP2, β3-adrenergic receptor, and PPARγ) (Sartipy, P. et al., *Proc. Natl. Acad. Sci. USA*, 96:6902 (1999)). Patients with type 2 diabetes had greater levels of circulating MCP-1 than non-diabetic controls (Nomura, S. et al., *Clin. Exp. Immunol.*, 121:437 (2000)), and release of MCP-1 from adipose tissue could be reduced by treatment with anti-diabetic therapies such as metformin or thiazolidinediones (Bruun, J. M. et al., *J. Clin. Endocrinol. Metab.*, 90:2282 (2005)). Likewise, MCP-1 was also overexpressed in murine experimental models of obesity, and was primarily produced by adipose tissue (Sartipy et al., *Proc. Natl. Acad. Sci. USA*, 100:7265 (2003)). In obese mice, the expression of MCP-1 both preceded and occurred concurrently with the onset of insulin resistance (Xu, H. et al., *J. Clin. Invest.*, 112:1821 (2003)). Another study showed that the expression of MCP-1 positively correlated with body mass in the perigonadal adipose tissue of mice (Weisberg et al., *J. Clin. Invest.*, 112:1796 (2003)). Consistent with these data, the development of insulin resistance in db/db mice was ameliorated either via genetic deletion of MCP-1 or by gene-induced expression of a dominant negative peptide (Kanda, H. et al., *J. Clin. Invest.*, 116:1494 (2006)). The logical converse could also be demonstrated: overexpression of MCP-1 in adipose tissue promoted insulin resistance (Kamei, N. et al., *J. Biol. Chem.*, 281:26602 (2006)). One conflicting result showing that genetic deletion of MCP-1 does not effect insulin resistance in the db/db mouse has also appeared (Chow, F. Y. et al., *Diabetologia*, 50:471 (2007)). Consistent with the data on MCP-1, direct studies with CCR-2 (the MCP-1 receptor) have showed that it plays a role in the formation of obesity and obesity-induced insulin resistance. Maintenance of a high fat diet increased the numbers of circulating CCR-2$^+$ inflammatory monocytes in both wild-type (Tsou, C. L. et al., *J. Clin. Invest.*, 117:902 (2007)) and ApoE–/– mice (Tacke, F. et al., *J. Clin. Invest.*, 117:185 (2007)). Genetic deletion of CCR-2 reduced numbers of activated macrophages in murine adipose tissue (Lumeng, C. N. et al., *Diabetes*, 56:16 (2007)), but did not affect a population of M2 adipose macrophages thought to maintain the "lean" state (Lumeng, C. N. et al., *J. Clin. Invest.*, 117:175 (2007)). Genetic deletion of CCR-2 reduced diet-induced obesity and improved insulin sensitivity in diet-induced obesity model (Weisberg, S. P. et al., *J. Clin. Invest.*, 116:115 (2006); Cornelius, P. et al., PCT Publication No. WO 2006/013427 A2), depending on experimental conditions (Chen, A. et al., *Obes. Res.*, 13:1311 (2005)). Administration of a small molecule CCR-2 antagonist also improved insulin sensitivity in this same model (Weisberg, S. P. et al., *J. Clin. Invest.*, 116:115 (2006)).

Two studies described the important role of CCR-2 in hypertension-induced vascular inflammation, remodeling, and hypertrophy (Bush, E. et al., *Hypertension*, 36:360 (2000); Ishibashi, M. et al., *Circ. Res.*, 94:1203 (2004)).

It is known that MCP-1 is upregulated in human multiple sclerosis, and it has been shown that effective therapy with interferon β-1b reduces MCP-1 expression in peripheral blood mononuclear cells, suggesting that MCP-1 plays a role in disease progression (Iarlori, C. et al., *J. Neuroimmunol.*, 123:170-179 (2002)). Other studies have demonstrated the potential therapeutic value of antagonism of the MCP-1/CCR-2 interaction in treating multiple sclerosis; all of these studies have been demonstrated in experimental autoimmune encephalomyelitis (EAE), the conventional animal model for multiple sclerosis. Administration of antibodies for MCP-1 to animals with EAE significantly diminished disease relapse (Kennedy, K. J. et al., *J. Neuroimmunol.*, 92:98 (1998)). Furthermore, two reports have shown that CCR-2–/– mice are resistant to EAE (Fife, B. T. et al., *J. Exp. Med.*, 192:899 (2000); Izikson, L. et al., *J. Exp. Med.*, 192:1075 (2000)). A subsequent report extended these initial observations by examining the effects of CCR-2 deletion in mice from different strains (Gaupp, S. et al., *Am. J. Pathol.*, 162:139 (2003)). Notably, administration of a small molecule CCR-2 antagonist also blunted disease progression in C57BL/6 mice (Brodmerkel, C. M. et al., *J. Immunol.*, 175:5370 (2005)).

It is known that MCP-1 is upregulated in patients who develop bronchiolitis obliterans syndrome after lung transplantation (Reynaud-Gaubert, M. et al., *J. Heart Lung Transplant.*, 21:721-730 (2002); Belperio, J. et al., *J. Clin. Invest.*, 108:547-556 (2001)). In a murine model of bronchiolitis obliterans syndrome, administration of an antibody to MCP-1 led to attenuation of airway obliteration; likewise, CCR-2–/– mice were resistant to airway obliteration in this same model (Belperio, J. et al., *J. Clin. Invest.*, 108:547-556 (2001)). These data suggest that antagonism of MCP-1/CCR-2 may be beneficial in treating rejection of organs following transplantation. In addition, studies have shown that disruption of MCP-1/CCR-2 axis was able to prolong the survival of islet transplant (Lee, I. et al., *J. Immunol.*, 171:6929 (2003); Abdi, R. et al., *J. Immunol.*, 172:767 (2004)). In rat graft models, CCR-2 and MCP-1 was shown to be upregulated in grafts that develop graft vasculopathy (Horiguchi, K. et al., *J. Heart Lung Transplant.*, 21:1090 (2002)). In another study, anti-MCP-1 gene therapy attenuated graft vasculopathy (Saiura, A. et al., *Arterioscler. Thromb. Vasc. Biol.*, 24:1886 (2004)). One study described inhibition of experimental vein graft neoinitimal formation by blockage of MCP-1 (Tatewaki, H. et al., *J. Vasc. Surg.*, 45:1236 (2007)).

Other studies have demonstrated the potential therapeutic value of antagonism of the MCP-1/CCR-2 interaction in treating asthma. Sequestration of MCP-1 with a neutralizing antibody in ovalbumin-challenged mice resulted in marked decrease in bronchial hyperresponsiveness and inflammation (Gonzalo, J.-A. et al., *J. Exp. Med.*, 188:157 (1998)). It proved possible to reduce allergic airway inflammation in *Schistosoma mansoni* egg-challenged mice through the administration of antibodies for MCP-1 (Lukacs, N. W. et al., *J. Immunol.*, 158:4398 (1997)). Consistent with this, MCP-1–/– mice displayed a reduced response to challenge with *Schistosoma mansoni* egg (Lu, B. et al., *J. Exp. Med.*, 187:601 (1998)).

Other studies have demonstrated the potential therapeutic value of antagonism of the MCP-1/CCR-2 interaction in treating kidney disease. Administration of antibodies for MCP-1 in a murine model of glomerularnephritis resulted in a marked decrease in glomerular crescent formation and deposition of type I collagen (Lloyd, C. M. et al., *J. Exp. Med.*, 185:1371 (1997)). In addition, MCP-1–/– mice with induced nephrotoxic serum nephritis showed significantly less tubular damage than their MCP-1+/+ counterparts (Tesch, G. H. et al., *J. Clin. Invest.*, 103:73 (1999)).

Several studies have demonstrated the potential therapeutic value of antagonism of the MCP-1/CCR-2 interaction in treating systemic lupus erythematosus. CCR-2–/– mice exhibited prolonged survival and reduced renal disease relative to their WT counterparts in a murine model of systemic lupus erythematosus (Perez de Lema, G. et al., *J. Am. Soc. Neph.*, 16:3592 (2005)). These data are consistent with the disease-modifying activity found in recent studies on genetic deletion of MCP-1 (Shimizu, S. et al., *Rheumatology* (Oxford), 43:1121 (2004); Tesch, G. H. et al., *J. Exp. Med.*, 190:1813 (1999)) or administration of a peptide antagonist of CCR-2 (Hasegawa, H. et al., *Arthritis Rheum.*, 48:2555 (2003)) in rodent models of lupus.

A remarkable 30-fold increase in CCR-2$^+$ lamina propria lymphocytes was observed in the small bowels from Crohn's patients relative to non-diseased ileum (Connor, S. J. et al., *Gut*, 53:1287 (2004)). Also of note, there was an expansion in the subset of circulating CCR-2$^+$/CD14$^+$/CD56$^+$ monocytes in patients with active Crohn's disease relative to controls. Several rodent studies have demonstrated the potential therapeutic value of antagonism of the MCP-1/CCR-2 interaction in treating Crohn's disease/colitis. CCR-2–/– mice were protected from the effects of dextran sodium sulfate-induced colitis (Andres, P. G. et al., *J. Immunol.*, 164:6303 (2000)). Administration of a small molecule antagonist of CCR-2, CCR-5, and CXCR3 (murine binding affinities=24, 236, and 369 nM, respectively) also protected against dextran sodium sulfate-induced colitis (Tokuyama, H. et al., *Int. Immunol.*, 17:1023 (2005)). Finally, MCP-1–/– mice showed substantially reduced colonic damage (both macroscopic and histological) in a hapten-induced model of colitis (Khan, W. I. et al., *Am. J. Physiol. Gastrointest. Liver Physiol.*, 291:G803 (2006)).

Two reports described the overexpression of MCP-1 in the intestinal epithelial cells and bowel mucosa of patients with inflammatory bowel disease (Reinecker, H. C. et al., *Gastroenterology*, 108:40 (1995), and Grimm, M. C. et al., *J. Leukoc. Biol.*, 59:804 (1996)).

One study described the association of promoter polymorphism in the MCP-1 gene with scleroderma (systemic sclerosis) (Karrer, S. et al., *J. Invest. Dermatol.*, 124:92 (2005)). In related models of tissue fibrosis, inhibition of CCR-2/MCP-1 axis reduced fibrosis in skin (Yamamoto, T. et al., *J. Invest. Dermatol.*, 121:510 (2003); Ferreira, A. M. et al., *J. Invest. Dermatol.*, 126:1900 (2006)), lung (Okuma, T. et al., *J. Pathol.*, 204:594 (2004); Gharaee-Kermani, M. et al., *Cytokine*, 24:266 (2003)), kidney (Kitagawa, K. et al., *Am. J. Pathol.*, 165:237 (2004); Wada, T. et al., *J. Am. Soc. Nephrol.*, 15:940 (2004)), heart (Hayashidani, S. et al., *Circulation*, 108:2134 (2003)), and liver (Tsuruta, S. et al., *Int. J. Mol. Med.*, 14:837 (2004)).

One study has demonstrated the potential therapeutic value of antagonism of the MCP-1/CCR-2 interaction in treating alveolitis. When rats with IgA immune complex lung injury were treated intravenously with antibodies raised against rat MCP-1 (JE), the symptoms of alveolitis were partially alleviated (Jones, M. L. et al., *J. Immunol.*, 149:2147 (1992)).

Several studies have shown the potential therapeutic value of antagonism of the MCP-1/CCR-2 interaction in treating cancer (reviewed in: Craig, M. J. et al., *Cancer Metastasis Rev.*, 25:611 (2006); Conti, I. et al., *Seminars in Cancer Biology*, 14:149 (2004); Giles, R. et al., *Curr. Cancer Drug Targets*, 6:659 (2006)). When immunodeficient mice bearing human breast carcinoma cells were treated with an anti-MCP-1 antibody, inhibition of lung micrometastases and increases in survival were observed (Salcedo, R. et al., *Blood*, 96:34-40 (2000)). Using human clinical tumor specimens, CCR-2 expression was associated with prostrate cancer progression (Lu, Y. et al., *J. Cell. Biochem.*, 101:676 (2007)). In vitro, MCP-1 expression has been shown to mediate prostrate cancer cell growth and invasion (Lu, Y. et al., *Prostate*, 66:1311 (2006)); furthermore, MCP-1 expressed by prostate cancer cells induced human bone marrow progenitors for bone resorption (Lu, Y. et al., *Cancer Res.*, 67:3646 (2007)).

Multiple studies have described the potential therapeutic value of antagonism of the MCP-1/CCR-2 interaction in treating restenosis. In humans, MCP-1 levels correlate directly with risk for restenosis (Cipollone, F. et al., *Arterioscler. Thromb. Vasc. Biol.*, 21:327 (2001)). Mice deficient in CCR-2 or in MCP-1 showed reductions in the intimal area and in the intima/media ratio (relative to wildtype littermates) after arterial injury (Roque, M. et al., *Arterioscler. Thromb. Vasc. Biol.*, 22:554 (2002); Schober, A. et al., *Circ. Res.*, 95:1125 (2004); Kim, W. J. et al., *Biochem. Biophys. Res. Commun.*, 310:936 (2003)). In mice, transfection of a dominant negative inhibitor of MCP-1 in the skeletal muscle (Egashira, K. et al., *Circ. Res.*, 90:1167 (2002)) also reduced intimal hyperplasia after arterial injury. Blockade of CCR-2 using a neutralizing antibody reduced neointimal hyperplasia after stenting in primates (Horvath, C. et al., *Circ. Res.*, 90:488 (2002)).

Two reports describe the overexpression of MCP-1 rats with induced brain trauma (King, J. S. et al., *J. Neuroimmunol.*, 56:127 (1994), and Berman, J. W. et al., *J. Immunol.*, 156:3017 (1996)). In addition, studies have shown that both CCR-2–/– (Dimitrijevic, O. B. et al., *Stroke*, 38:1345 (2007)) and MCP-1–/– mice (Hughes, P. M. et al., *J. Cereb. Blood Flow Metab.*, 22:308 (2002)) are partially protected from ischemia/reperfusion injury.

It is known that monocytes/macrophages play an important role in the development of neuropathic pain (Liu, T. et al., *Pain*, 86:25 (2000)). Consistent with this notion, a potential role for CCR-2 in the treatment of both inflammatory and neuropathic pain has been described recently. CCR-2–/– mice showed altered responses to inflammatory pain relative to their WT counterparts, including reduced pain behavior after intraplantar formalin injection and slightly reduced mechanical allodynia after intraplantar CFA injection (Abbadie, C. et al., *Proc. Natl. Acad. Sci. USA*, 100:7947 (2003)). In addition, CCR-2–/– mice did not display significant mechanical allodynia after sciatic nerve injury. Likewise, a small molecule CCR-2 antagonist reduced mechanical allodynia to ~80% of pre-injury levels after oral administration (Abbadie, C. et al., PCT Publication No. WO 2004/110376).

One study described the critical role of MCP-1 in ischemic cardiomyopathy (Frangogiannis, N. G. et al., *Circulation*, 115:584 (2007)). Another study described the attenuation of experimental heart failure following inhibition of MCP-1 (Hayashidani, S. et al., *Circulation*, 108:2134 (2003)).

Other studies have provided evidence that MCP-1 is overexpressed in various disease states not mentioned above. These reports provide correlative evidence that MCP-1 antagonists could be useful therapeutics for such diseases. Another study has demonstrated the overexpression of MCP-1 in rodent cardiac allografts, suggesting a role for MCP-1 in the pathogenesis of transplant arteriosclerosis (Russell, M. E. et al., *Proc. Natl. Acad. Sci. USA*, 90:6086 (1993)). The overexpression of MCP-1 has been noted in the lung endothelial cells of patients with idiopathic pulmonary fibrosis (Antoniades, H. N. et al., *Proc. Natl. Acad. Sci. USA*, 89:5371 (1992)). Similarly, the overexpression of MCP-1 has been noted in the skin from patients with psoriasis (Deleuran, M. et al., *J. Dermatol. Sci.*, 13:228 (1996), and Gillitzer, R. et al., *J. Invest. Dermatol.*, 101:127 (1993)); correlative findings with predominance of CCR-2+ cells have also been reported (Vestergaard, C. et al., *Acta Derm. Venerol.*, 84:353 (2004)). Finally, a recent report has shown that MCP-1 is overexpressed in the brains and cerebrospinal fluid of patients with HIV-1-associated dementia (Garzino-Demo, A., PCT Publication No. WO 99/46991).

In addition, CCR-2 polymorphism has been shown to be associated with sarcoidosis at least in one subset of patients (Spagnolo, P. et al., *Am. J. Respir. Crit. Care Med.*, 168:1162 (2003)).

It should also be noted that CCR-2 has been implicated as a co-receptor for some strains of HIV (Doranz, B. J. et al., *Cell*, 85:1149 (1996)). It has also been determined that the use of CCR-2 as an HIV co-receptor can be correlated with disease progression (Connor, R. I. et al., *J. Exp. Med.*, 185:621 (1997)). This finding is consistent with the recent finding that the presence of a CCR-2 mutant, CCR-2-64I, is positively correlated with delayed onset of HIV in the human population (Smith, M. W. et al., *Science*, 277:959 (1997)). Although MCP-1 has not been implicated in these processes, it may be that MCP-1 antagonists that act via binding to CCR-2 may have beneficial therapeutic effects in delaying the disease progression to AIDS in HIV-infected patients.

It should be noted that CCR-2 is also the receptor for the human chemokines MCP-2, MCP-3, and MCP-4 (Luster, *New Eng. J. Med.*, 338:436-445 (1998)). Since the new compounds of formula (I) described herein antagonize MCP-1 by binding to the CCR-2 receptor, it may be that these compounds of formula (I) are also effective antagonists of the actions of MCP-2, MCP-3, and MCP-4 that are mediated by CCR-2. Accordingly, when reference is made herein to "antagonism of MCP-1," it is to be assumed that this is equivalent to "antagonism of chemokine stimulation of CCR-2."

Accordingly, compounds that modulate chemokine activity could demonstrate a wide range of utilities in treating inflammatory, allergic, autoimmune, metabolic, cancer and/or cardiovascular diseases. PCT Publication Nos. WO 2005/021500 A1 (incorporated herein by reference and assigned to present applicant), WO 2008/014381 A1, WO 2008/014360 A1 and WO 2008/014361 A1, disclose compounds that modulate MCP-1, MCP-2, MCP-3 and MCP-4 activity via CCR-2. The references also disclose various processes to prepare these compounds including multistep syntheses that include the introduction and subsequent removal of protecting groups.

It is desirable to find new compounds with improved pharmacological characteristics compared with known chemokine modulators. For example, it is desirable to find new compounds with equipotent dual CCR-2/5 inhibitory activity in comparison to selectivity for CCR-2 alone, predominantly CCR-2 versus CCR-5, predominantly CCR-5 versus CCR-2, or other G protein-coupled receptors (i.e., 5HT2A receptor). It is also desirable to find compounds with equipotent dual CCR-2/5 inhibitory activity and advantageous characteristics in one or more of the following categories:

(a) pharmaceutical properties (i.e., solubility, permeability, amenability to sustained release formulations);

(b) dosage requirements (e.g., lower dosages and/or once-daily dosing);

(c) factors which decrease blood concentration peak-to-trough characteristics (i.e., clearance and/or volume of distribution);

(d) factors that increase the concentration of active drug at the receptor (i.e., protein binding, volume of distribution);

(e) factors that decrease the liability for clinical drug-drug interactions (cytochrome P450 enzyme inhibition or induction, such as CYP 2D6 inhibition, see Dresser, G. K. et al., *Clin. Pharmacokinet.*, 38:41-57 (2000), which is hereby incorporated by reference); and (f) factors that decrease the potential for adverse side-effects (e.g., pharmacological selectivity beyond G protein-coupled receptors, potential chemical or metabolic reactivity, limited CNS penetration, ion-channel selectivity). It is especially desirable to find compounds having a desirable combination of the aforementioned pharmacological characteristics.

It is also desirable in the art to provide new and/or improved processes to prepare such compounds. These processes may be characterized, without limitation, by a) facile adaptation to larger scale production, such as pilot plant or manufacturing scales; b) process steps and/or techniques enabling improvements in the purity (including chiral purity), stability and/or ease of handling of intermediates and/or final compounds; and/or c) fewer process steps.

BRIEF SUMMARY OF THE INVENTION

The present invention provides a novel antagonist: N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, or a pharmaceutically acceptable salt, solvate or prodrug, thereof, having unexpected equipotent dual CCR-2 and CCR-5 receptor inhibitory activity. In addition, the present invention presents a novel and unexpected combination of equipotent dual CCR-2/5 activity and desirable pharmacological characteristics. Crystalline and metabolite forms of the present invention are also provided. Pharmaceutical compositions containing the same and methods of using the same as agents for the treatment of inflammatory diseases, allergic, autoimmune, metabolic, cancer and/or cardiovascular diseases is also an objective of this invention. The present disclosure also provides a process for preparing compounds of Formula (I), including N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide:

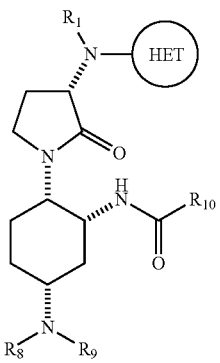

I wherein $R^1$, $R^8$, $R^9$, $R^{10}$, and

are as described herein. Compounds that are useful intermediates of the process are also provided herein.

The present disclosure also provides the use of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, N-((1R,2S,5R)-5-(tert-butylamino)-2-((S)-3-(7-(2-hydroxy-1,1-dimethyl-ethyl)pyrazolo[1,5-a][1,3,5]triazin-4-ylamino)-2-oxopyrrolidin-1-yl)cyclohexyl) acetamide, or a pharmaceutically acceptable salt, solvate or prodrug, for the manufacture of a medicament for the treatment of inflammatory diseases, allergic, autoimmune, metabolic, cancer and/or cardiovascular diseases.

The present disclosure also provides metabolites of active compounds, or pharmaceutically acceptable salts or prodrugs thereof, pharmaceutical compositions thereof and methods of using the metabolites in the treatment of inflammatory, allergic, autoimmune, metabolic, cancer and/or cardiovascular diseases, particularly diabetes, multiple sclerosis, Crohn's disease and/or atherosclerosis.

Accordingly, disclosed herein are novel modulators of chemokine activity, or pharmaceutically acceptable salts or prodrugs thereof, having an unexpected combination of desirable pharmacological characteristics.

The present disclosure provides pharmaceutical compositions comprising a pharmaceutically acceptable carrier and a therapeutically effective amount of at least one of the compounds of the present invention or a pharmaceutically acceptable salt or prodrug form thereof.

The present disclosure also provides methods for treating inflammatory, allergic, autoimmune, metabolic, cancer and/or cardiovascular diseases, particularly diabetes, multiple sclerosis, Crohn's disease and/or atherosclerosis, comprising administering to a host in need of such treatment a therapeutically effective amount of at least one of the compounds of the present invention, or a pharmaceutically acceptable salt or prodrug form thereof.

The present disclosure provides a process for preparing compounds disclosed herein and intermediates useful therefore.

The present disclosure provides for the use of the compounds of the present invention in therapy.

The present disclosure provides the use of compounds of the present invention for the manufacture of a medicament for the treatment of inflammatory, allergic, autoimmune, metabolic, cancer and/or cardiovascular diseases.

DETAILED DESCRIPTION OF THE INVENTION

Figure 1:
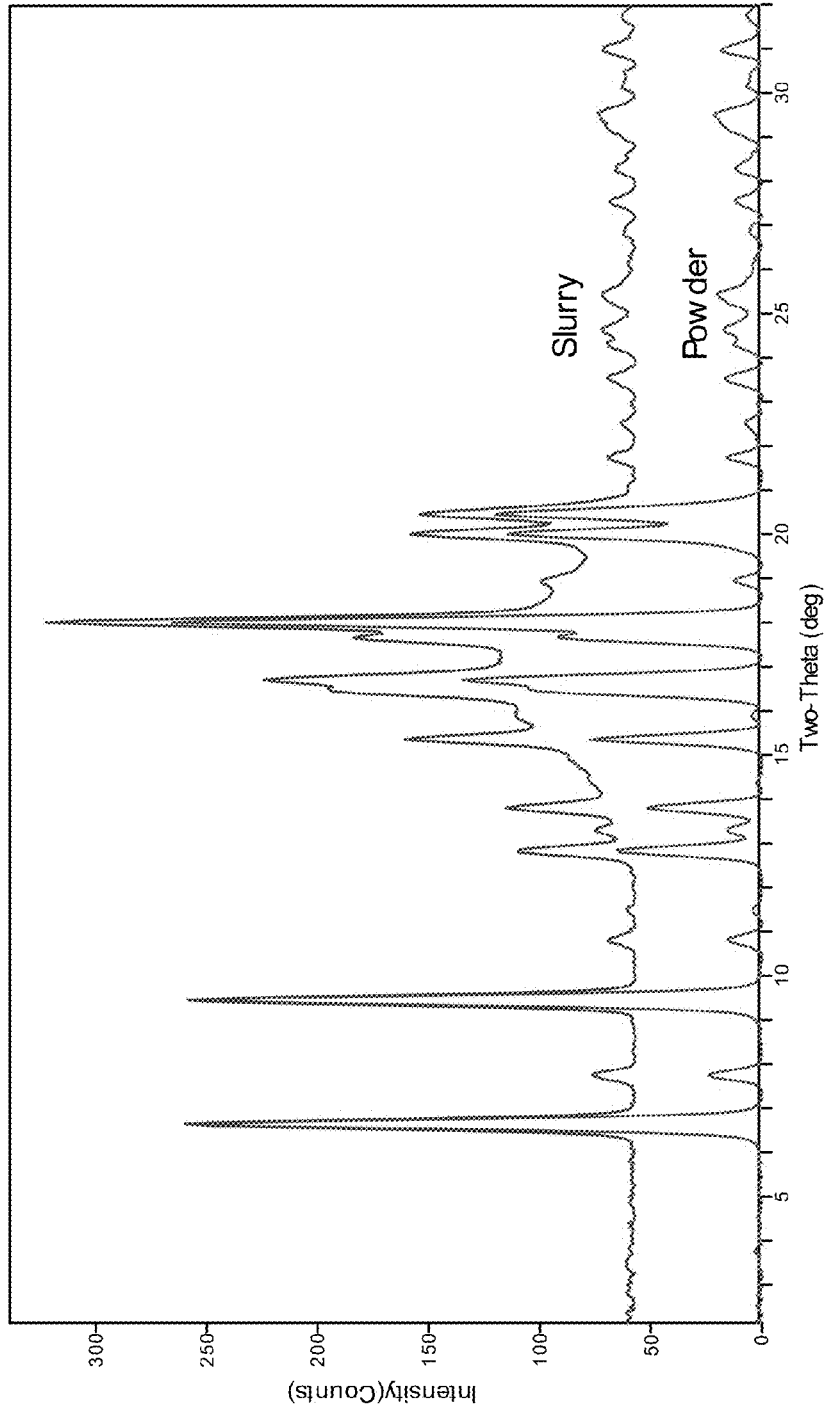
FIG. 1 discloses the experimental and simulated powder patterns of the N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide.

The present invention provides a novel antagonist: N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, or a pharmaceutically acceptable salt, solvate or prodrug, thereof, having unexpected equipotent dual CCR-2 and CCR-5 receptor activity. Additionally, the present invention provides a novel combination of desirable pharmacological characteristics. Crystalline forms and metabolites of the present invention are also provided. Pharmaceutical compositions containing the same and methods of using the same as agents for the treatment of inflammatory diseases, allergic, autoimmune, metabolic, cancer and/or cardiovascular diseases is also an objective of this invention. The present disclosure also provides a process for preparing compounds of Formula (I), including N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide:

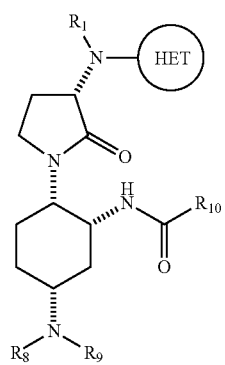

I wherein $R^1$, $R^8$, $R^9$, $R^{10}$, and

are as described herein. Compounds that are useful intermediates of the process are also provided herein.

N-((1R,2S,5R)-5-(tert-Butylamino)-2-((S)-3-(7-tert-butylpyrazolo[1,5-a][1,3,5]triazin-4-ylamino)-2-oxopyrrolidin-1-yl)cyclohexyl)acetamide, unexpectedly demonstrates equipotent dual CCR-2/5 receptor inhibitory activity.

Additionally, N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide demonstrates a desirable combination of equipotent dual CCR-2/5 receptor inhibitory activity and pharmacological characteristics including a surprisingly high degree of oral bioavailability in combination with indications that it is highly efficacious and has excellent safety criteria.

Known modulators of chemokine receptors, such as those disclosed in PCT Publication Nos. WO 2004/071460 A1 and WO 2005/021500 A1 (U.S. Pat. No. 7,163,937, issued Jan. 16, 2007, assigned to present Applicant) are not sufficiently efficacious, as measured by their CCR-2 or CCR-5-binding ability (a measure of efficacy), and/or they lack appropriate criteria for safety as indicated by ion channel selectivity as measured by hERG and Na+ ion channel studies.

Other known modulators of chemokine receptors, such as those disclosed in PCT Publication Nos. WO 2008/014381 A1, WO 2008/014360 A1 and WO 2008/014361 A1, are selective as antagonist or partial agonist/antagonist of CCR-2 receptor activity. However, these known modulators demonstrate predominantly CCR-2 activity and are not equipotent dual antagonists, as measured by their CCR-2 and CCR-5-binding ability.

Other known modulators of chemokine receptors, such as those disclosed by Carter et al. (*American Chemical Society*, Aug. 17, 2008) are dual CCR-2/5 modulators but lack appropriate criteria for safety as indicated by ion channel selectivity as measured by hERG and Na+ ion channel studies.

In contrast, as illustrated by the data presented herein in the section titled "Comparative Pharmacological Characteristics", infra, N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide surprisingly exhibits equipotent CCR-5 and CCR-2 binding ability. In addition, N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide demonstrates a surprisingly high degree of membrane permeability, and yet maintains equipotent CCR-2/5 dual binding ability along with excellent ion channel selectivity.

Accordingly, the present invention provides new chemokine modulators having equipotent CCR-2 and CCR-5 binding ability and improves pharmacological characteristics that are expected to be useful in treating inflammatory, allergic, autoimmune, metabolic, cancer and/or cardiovascular diseases.

EMBODIMENTS

In one embodiment, the disclosure is directed to N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide:

and pharmaceutically acceptable salts, thereof.

Another embodiment is a crystalline form of N-((1R,2S, 5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide.

Another embodiment is a crystalline form of N-((1R,2S, 5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, wherein the crystalline form comprises the N-1 and/or P-1 Form.

Another embodiment is a crystalline form of N-((1R,2S, 5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, wherein the crystalline form comprises the N-1 Form.

Another embodiment is a crystalline form of N-((1R,2S, 5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, wherein the crystalline form comprises the N-1 or P-1 Form in substantially pure form.

Another embodiment is a crystalline form of N-((1R,2S, 5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, wherein the crystalline form comprises the N-1 Form in substantially pure form.

Another embodiment is the N-1 Form characterized by unit cell parameters substantially equal to the following:
Cell Dimensions:
a=7.3085(6)
b=16.257(1)
c=22.688(2)
α°=90
β°=90
γ°=90
Space group $P2_12_12_1$
Molecules/unit cell (Z): 1
Density, calc g-cm$^{-3}$: 1.194
wherein said crystal is at a temperature of about −70° C.

Another embodiment is the N-2 Form characterized by (or having) a power x ray diffraction pattern substantially according to FIG. 1.

Figure 2:
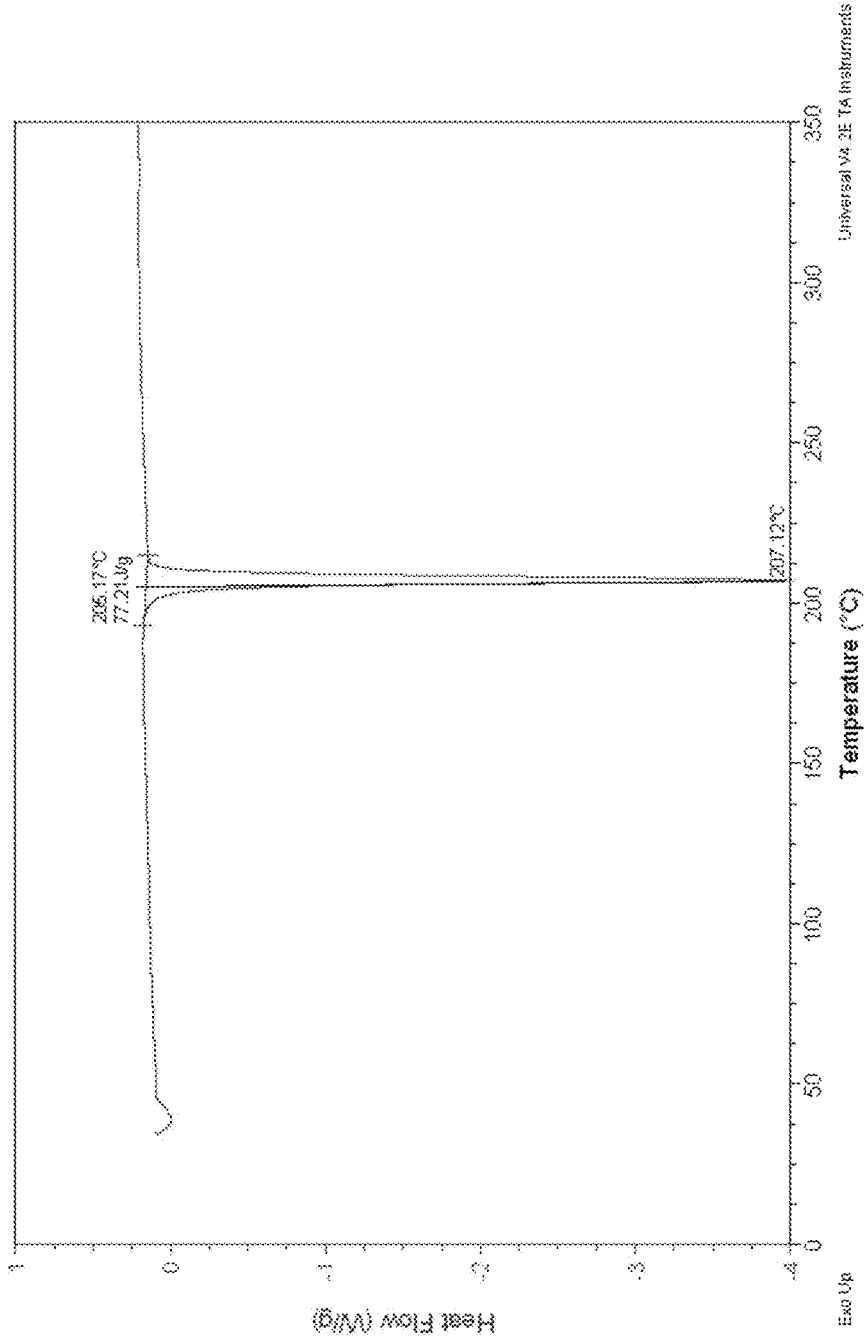
FIG. 2 discloses the differential scanning calorimetry analysis of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, free base Form N-1.

Another embodiment is the N-2 Form characterized by (or having) a differential scanning calorimetry thermogram substantially in accordance with that shown in FIG. 2, having an endothermic transition above ca. 205° C.

Figure 3:
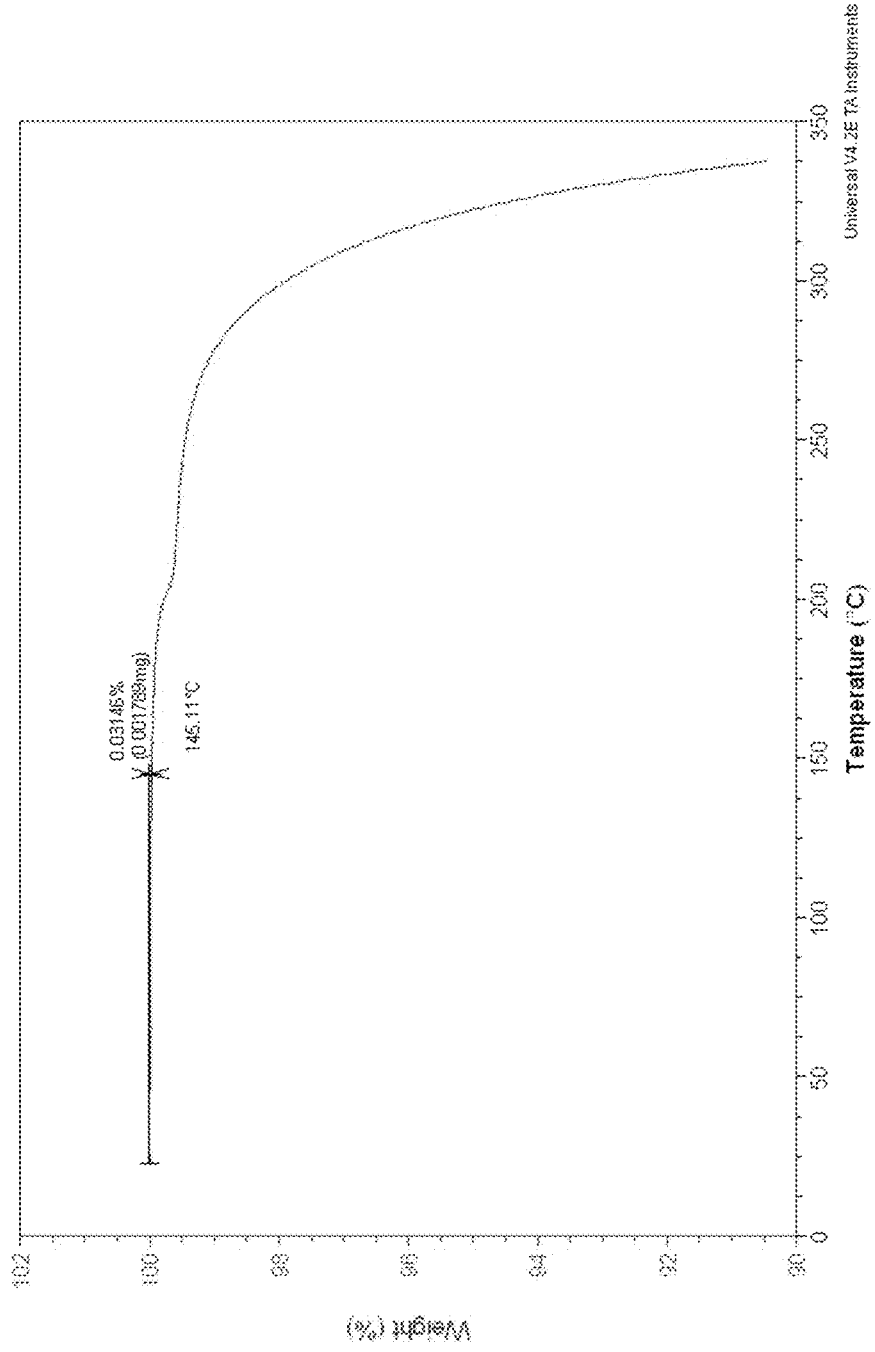
FIG. 3 discloses the thermogravimetric analysis of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, free base Form N-1.

Another embodiment is characterized by (or having) a thermal gravimetric analysis curve in accordance with that shown in FIG. 3.

Another embodiment is a crystalline form of N-((1R,2S, 5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, comprising Form N-1, characterized by the unit cell parameters found in Table 1; and/or a powder x-ray diffraction pattern substantially according to FIG. 1.

Another embodiment is a pharmaceutical composition comprised of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a pharmaceutical composition comprised of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, pharmaceutically acceptable salts, thereof, and a pharmaceutically acceptable carrier.

Another embodiment is a pharmaceutical composition comprised of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, pharmaceutically acceptable salts, thereof, and at least one additional therapeutic agent.

Another embodiment is a method for modulating chemokine or chemokine receptor activity comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of modulating CCR-2 and CCR-5 receptor activity comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method modulating MCP-1, MCP-2, MCP-3, MCP-4, MCP-5, MIP-1a, MIP-1b and RANTES activity that is mediated by the CCR-2 and CCR-5 receptor comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of modulating MCP-1 activity comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating a disorder, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof, said the disorder is selected from diabetes, obesity, metabolic syndrome, stroke, neuropathic pain, ischemic cardiomyopathy, psoriasis, hypertension, scleroderma, osteoarthritis, aneurism, fever, cardiovascular disease, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, vasculitis, vulnerable plaques, rheumatoid arthritis, restenosis, venous neointimal hyperplasia, dialysis-graft neointimal hyperplasia, arterio-venous shunt intimal hyperplasia, organ transplantation, chronic allograft nephropathy, and cancer.

Another embodiment is a method of treating a disorder, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof, wherein said disorder is selected from diabetes, obesity, Crohn's disease, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, and rheumatoid arthritis, restenosis, organ transplantation, cancer, venous neointimal hyperplasia, dialysis-graft neointimal hyperplasia, and arterio-venous shunt neointimal hyperplasia.

Another embodiment is a method of treating a disorder, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof, wherein said disorder is selected from diabetes, obesity, Crohn's disease, systemic lupus erythematosus, glomerulonephritis, multiple sclerosis, atherosclerosis, restenosis, organ transplantation, venous neointimal hyperplasia, dialysis-graft neointimal hyperplasia, and arterio-venous shunt neointimal hyperplasia.

Another embodiment is a method of treating a disorder, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof, wherein said disorder is selected from multiple sclerosis, atherosclerosis, Crohn's disease, diabetes, venous neointimal hyperplasia, dialysis-graft neointimal hyperplasia, and arterio-venous shunt neointimal hyperplasia.

Another embodiment is a method of treating a disorder, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof, wherein said disorder is being selected from restenosis, organ transplantation, cancer, venous neointimal hyperplasia, dialysis-graft neointimal hyperplasia, and arterio-venous shunt neointimal hyperplasia.

Another embodiment is a method of treating diabetes, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating Crohn's disease, comprising administering to a patient in need thereof a therapeutically effective amount of t N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating multiple sclerosis, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating atherosclerosis, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating restenosis, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating organ transplantation, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating cancer, for example, breast cancer, liver cancer, prostate cancer and melanoma, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating venous neointimal hyperplasia, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating dialysis-graft neointimal hyperplasia, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating arterio-venous shunt neointimal hyperplasia, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating an inflammatory disease, allergic, autoimmune, metabolic, and/or cardiovascular diseases comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of treating a disease which is at least partially mediated by CCR-2 and CCR-5, comprising administering to a patient in need thereof a therapeutically effective amount of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide and pharmaceutically acceptable salts, thereof.

Another embodiment is a method of using N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, and pharmaceutically acceptable salts, thereof, in the preparation of a medicament for the treatment of diabetes, obesity, metabolic syndrome, stroke, neuropathic pain, ischemic cardiomyopathy, psoriasis, hypertension, scleroderma, osteoarthritis, aneurism, fever, cardiovascular disease, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, vasculitis, vulnerable plaques, rheumatoid arthritis, restenosis, venous neointimal hyperplasia, dialysis-graft neointimal hyperplasia, arterio-venous shunt intimal hyperplasia, organ transplantation, chronic allograft nephropathy, cancer, venous neointimal hyperplasia, dialysis-graft neointimal hyperplasia, and arterio-venous shunt neointimal hyperplasia.

In yet another embodiment, the disclosure is directed to N-((1R,2S,5R)-5-(tert-butylamino)-2-((S)-3-(7-(2-hydroxy-1,1-dimethyl-ethyl)pyrazolo[1,5-a][1,3,5]triazin-4-ylamino)-2-oxopyrrolidin-1-yl)cyclohexyl)acetamide:

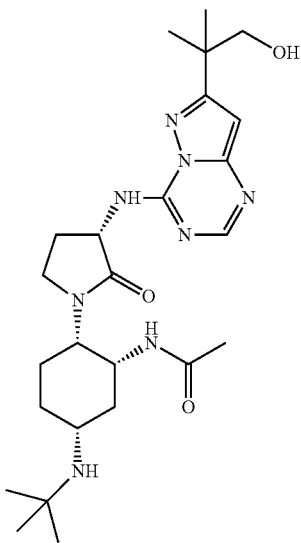 [SMILES: CC(=O)N[C@@H]1C[C@H](NC(C)(C)C)CC[C@@H]1N1CC[C@H](Nc2ncnc3cc(C(C)(C)CO)nn23)C1=O]

and pharmaceutically acceptable salts, thereof. Pharmaceutical compositions containing the same and methods of using the same as agents for the treatment of inflammatory diseases, allergic, autoimmune, metabolic, cancer and/or cardiovascular diseases is also an embodiment of this invention.

Process Embodiments

In a first embodiment, the disclosure provides a process for preparing a compound of formula I, or a salt form thereof:

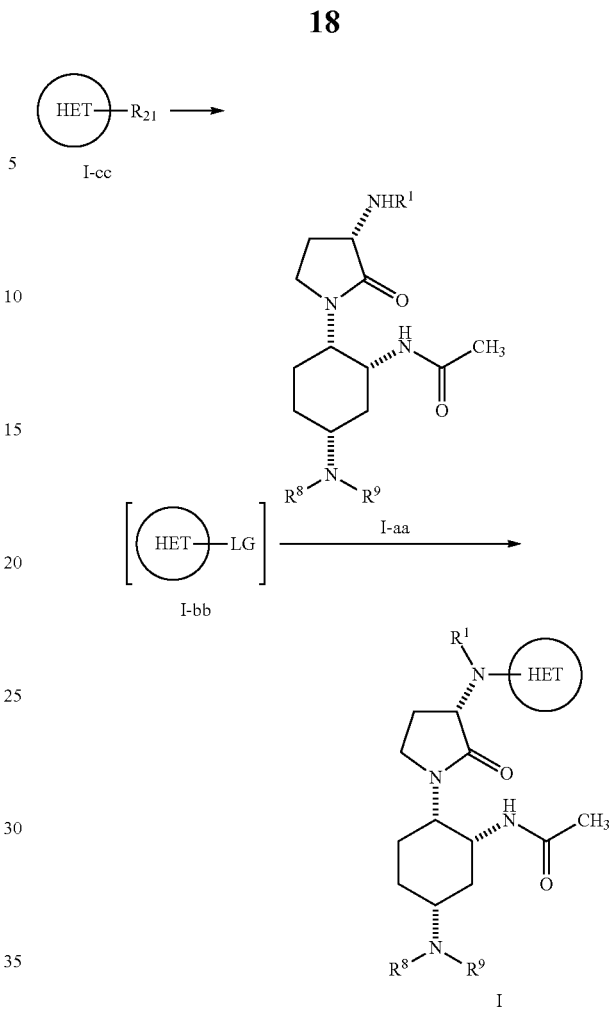

comprising:
1) converting a hydrazone compound of formula I-cc to a compound of formula I-bb; and
2) coupling the compound of formula I-bb with a compound of formula I-aa; wherein:
$R_1$ is independently hydrogen or an amine-protecting group selected from a carbobenzyloxy group, a tert-butyloxycarbonyl, a fluorenylmethyloxycarbonyl group, a benzyl group, and a p-methoxybenzyl group;
$R_8$ and $R_9$ are independently hydrogen or $C_{1-6}$alkyl;
$R_{21}$ is =O;
HET is an optionally substituted 3- to 14-membered heterocyclo or heteroaryl bicyclic ring having at least one nitrogen heteroatom; and
LG is —$OR_{16}$, wherein $R_{16}$ is $C_{1-6}$alkyl, phenyl, a 5- to 7-membered heteroaryl having one or more atoms selected from N, S, or O, or a 3- to 7-membered cycloalkyl, all of which are optionally substituted with 1 to 3 groups selected from halogen, $CF_3$ or $C_{1-6}$alkyl.

In a second embodiment, the disclosure provides a process wherein the compound of formula I is N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide.

In a third embodiment, the disclosure provides a process for preparing a compound of formula I wherein the compound of formula I-bb is a compound of the formula:

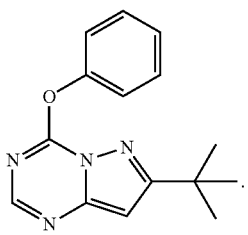 [SMILES: CC(C)(C)c1cc2ncnc(Oc3ccccc3)n2n1]

In a fourth embodiment, the disclosure provides a process for preparing a compound of formula I wherein the coupling occurs via an acidic work-up followed by the addition of a base.

In a fifth embodiment, the disclosure provides a process for preparing a compound of formula I wherein the acid in acidic work-up is selected from citric acid, tartaric acid, glycolic acid, and hydrochloric acid.

In a sixth embodiment, the disclosure provides a process for preparing a compound of formula I wherein the base is selected from $K_2HPO_4$, $Na_2HPO_4$, $NaHCO_3$ and $KHCO_3$.

In a seventh embodiment, the disclosure provides a process for preparing a compound of formula I wherein converting of the hydrazone compound of formula I-cc to the compound of formula I-bb comprises reacting the hydrazone compound of formula I-cc with an acylating agent, a nucleophile, and/or a tertiary amine base in a solvent followed by interception with either (i) an alcohol in the presence of a second tertiary amine base or (ii) an alkoxide to form the compound of formula I-bb.

In an eighth embodiment, the disclosure provides a process wherein the acylating agent is selected from phosphorus oxychloride, oxalyl chloride, thionyl chloride and phosgene, preferably phosphorus oxychloride.

In a ninth embodiment, the disclosure provides a process wherein the tertiary amine base is selected from triethylamine, N—N-diisopropyl-N-ethyl amine, tri-n-propylamine, N-methyl morpholine and 1,4-diazabicyclo[2.2.2]octane, preferably N—N-diisopropyl-N-ethyl amine.

In a tenth embodiment, the disclosure provides a process wherein the nucleophile is selected from dimethyl 4-aminopyridine, dimethylaniline, pyridine and lutidine, preferably dimethyl 4-aminopyridine.

In an eleventh embodiment, the disclosure provides a process wherein the amount of nucleophile used in the reaction is 2.0 to 4.0 equivalents, preferably, 3.0 equivalents.

In a twelfth embodiment, the disclosure provides a process wherein the alcohol or alkoxide is selected from phenol, pentafluorophenol, methanol, ethanol, sodium methoxide and sodium phenolate, preferably, phenol.

In a thirteenth embodiment, the present disclosure provides a process wherein the second tertiary amine base is selected from triethylamine, N—N-diisopropyl-N-ethyl amine, tri-n-propylamine, N-methyl morpholine, and 1,4-diazabicyclo[2.2.2]octane, preferably, N—N-diisopropyl-N-ethyl amine.

In a fourteenth embodiment, the disclosure provides a process wherein the solvent is selected from acetonitrile, dichloromethane and neat phosphorus oxychloride.

In a fifteenth embodiment, the disclosure provides a process wherein the reaction and interception is carried out at a temperature in the range of ambient temperature to 70° C.

In a sixteenth embodiment, the disclosure provides a process wherein the compound of formula I-cc is a compound of the formula:

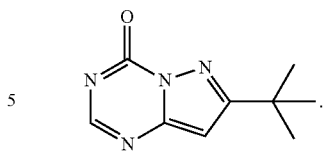

In a seventeenth embodiment, the present invention provides a process wherein the hydrazone compound formula I-cc is prepared by a process comprising reacting a hydrazone compound of formula I-dd

with orthoformate in the presence of an acid at elevated temperature to yield the hydrazone compound of formula I-cc; wherein $R_{21}$ is =O; $R_{22}$ is —NH—$NH_2$; and $R_{23}$ is cyanoalkyl; or $R_{22}$ and $R_{23}$ may be taken together to form a 5- to 8-membered ring, wherein the ring may be optionally substituted with one or more substituents selected from amino, alkyl, aryl, or heteroaryl and may optionally contain 1, 2, 3, or 4 heteroatoms independently selected from the group consisting of N, S, or O.

In an eighteenth embodiment, the disclosure provides a process wherein the orthoformate is selected from trimethylorthoformate, triethylorthoformate, and tripropylorthoformate, preferably, trimethylorthoformate.

In a nineteenth embodiment, the disclosure provides a process wherein the acid is selected from acetic acid, trifluoroacetic acid, hydrochloric acid and methanesulfonic acid, preferably, acetic acid.

In a twentieth embodiment, the disclosure provides a process wherein the reaction is carried out at a temperature in the range of 40-90° C., preferably, 40-75° C.

In a twenty-first embodiment, the disclosure provides a process wherein the compound of formula I-dd is selected from a compound of the formula:

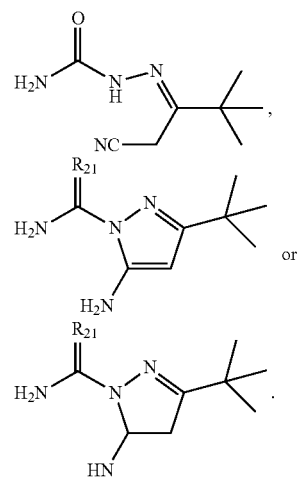

In a twenty-second embodiment, the disclosure provides a process wherein the hydrazone compound formula I-dd is prepared by a process comprising condensing a compound of formula I-ee, $R_{23}$=O, with a carbazide compound of formula I-ff:

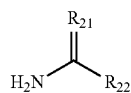

I-ff in a solvent in the presence of a base to yield the hydrazone compound of formula I-dd; wherein $R_{21}$ is =O and $R_{22}$ and $R_{23}$ are as set forth above.

In a twenty-third embodiment, the disclosure provides a process wherein the solvent is selected from ethanol, 2-propanol, 1-propanol and methanol, preferably, ethanol.

In a twenty-fourth embodiment, the disclosure provides a process wherein the base is selected from sodium acetate, potassium acetate, triethylamine and N—N-diisopropyl-N-ethyl amine, preferably, sodium acetate.

In a twenty-fifth embodiment, the disclosure provides a process wherein the condensation occurs at a temperature in the range of 20-60° C., preferably, 25-55° C.

In a twenty-sixth embodiment, the present invention provides a process wherein the carbazide compound of formula I-ff is semicarbazide hydrochloride.

In a twenty-seventh embodiment, the present invention provides a process wherein the compound of formula I-ee is pivaloyl acetonitrile.

In a twenty-eighth embodiment, the present invention provides a process for preparing N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide comprising the process set forth in the following scheme:

ered limiting. Any and all embodiments of the present invention may be taken in conjunction with any other embodiment or embodiments to describe additional embodiments. Each individual element (e.g., preferable or special aspects) of the embodiments is its own independent embodiment. Furthermore, any element of an embodiment is meant to be combined with any and all other elements from any embodiment to describe an additional embodiment. In addition, the present invention encompasses combinations of different embodiment, parts of embodiments, definitions, descriptions, and examples of the invention noted herein.

DEFINITIONS

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 6 carbon atoms. When numbers appear in a subscript after the symbol "C", the subscript defines with more specificity the number of carbon atoms that a particular group may contain. For example, "$C_{1-6}$alkyl" refers to straight and branched chain alkyl groups with 1 to 6 carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$)hydroxyalkyl includes hydroxy, hydroxymethyl and hydroxyethyl. Alkyl groups may be substituted with 1 to 3 groups selected from ($C_{1-6}$)alkyl, ($C_{2-6}$)alkenyl, hydroxy, halogen, cyano, nitro, $CF_3$, $O(C_{1-6}$alkyl), $OCF_3$, C(=O)H, C(=O)($C_{1-6}$alkyl), $CO_2$H, $CO_2(C_{1-6}$alkyl), $NHCO_2(C_{1-6}$alkyl), —S($C_{1-6}$alkyl), $NH_2$, NH($C_{1-6}$alkyl),

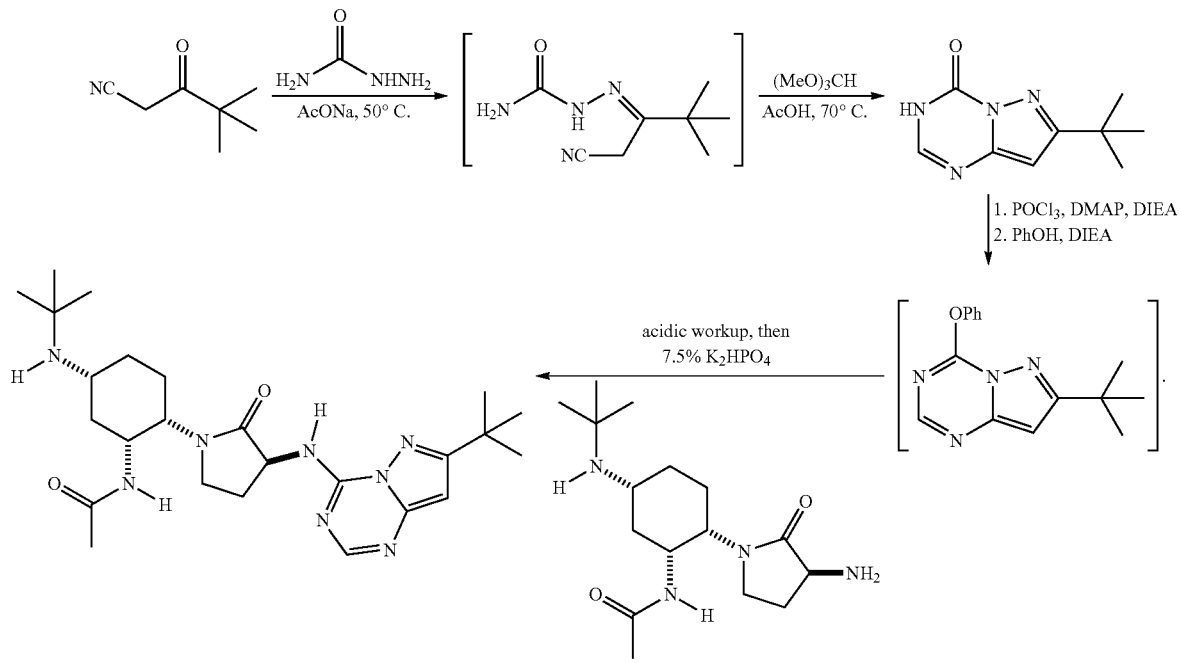

The present invention may be embodied in other specific forms without departing from the spirit or essential attributes thereof. Thus, the above embodiments should not be considered $N(C_{1-6}$alkyl$)_2$, $N(CH_3)_3^+$, $SO_2(C_{1-6}$alkyl), C(=O)($C_{1-4}$alkylene)$NH_2$, C(=O)($C_{1-4}$alkylene)NH(alkyl), C(=O)($C_{1-4}$alkylene)N($C_{1-4}$alkyl$)_2$, $C_{3-7}$cycloalkyl, phenyl, benzyl, phenylethyl, phenyloxy, benzyloxy, naphthyl, a 4- to 7-membered heterocyclo, and/or a 5- to 6-membered heteroaryl. When a substituted alkyl is substituted with an aryl, heterocyclo, cycloalkyl, or heteroaryl group, said ringed systems are as defined below and thus may have 0, 1, 2, or 3 substituents, also as defined below.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl ($C_{0-4}$)alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred. Alkenyl groups may be substituted as described above for alkyl groups.

The term "alkynyl" refers to straight or branched chain hydrocarbon groups having 2 to 12 carbon atoms and at least one triple bond. Alkynyl groups of 2 to 6 carbon atoms and having one triple bond are most preferred. Alkynyl groups may be substituted as described above for alkyl groups.

The term "alkylene" refers to bivalent straight or branched chain hydrocarbon groups having 1 to 12 carbon atoms, preferably 1 to 8 carbon atoms, e.g., {—$CH_2$—}$_n$, wherein n is 1 to 12, preferably 1 to 8. Lower alkylene groups, that is, alkylene groups of 1 to 2 carbon atoms, are most preferred. The terms "alkenylene" and "alkynylene" refer to bivalent radicals of alkenyl and alkynyl groups, respectively, as defined above. Alkenylene groups may be substituted as described above for alkyl groups.

The term "alkoxy" refers to an oxygen atom substituted by alkyl, as defined herein. For example, the term "alkoxy" or includes the group —O—$C_{1-6}$alkyl.

When a subscript is used with reference to an alkoxy, thioalkyl or aminoalkyl, the subscript refers to the number of carbon atoms that the group may contain in addition to heteroatoms.

It should be understood that the selections for all groups, including for examples, alkoxy, thioalkyl, and aminoalkyl, will be made by one skilled in the field to provide stable compounds.

The term "carbonyl" refers to a bivalent carbonyl group —C(=O)—.

The term "acyl" refers to a carbonyl group linked to an organic radical, more particularly, the group C(=O)$R_e$, as well as the bivalent group —C(=O)$R_e$—, which are linked to organic radicals. The group $R_e$ can be selected from alkyl, alkenyl, alkynyl, cycloalkyl, heterocyclo, aryl, or heteroaryl as defined herein, or when appropriate, the corresponding bivalent group, e.g., alkylene.

The term "cycloalkyl" refers to fully saturated and partially unsaturated hydrocarbon rings (and therefore includes "cycloalkenyl rings") of 3 to 9, preferably 3 to 7 carbon atoms. The term "cycloalkyl" includes such rings having 0, 1, 2, or 3 substituents selected from ($C_{1-4}$alkyl, ($C_{2-4}$alkenyl, halogen, hydroxy, cyano, nitro, $CF_3$, O($C_{1-4}$alkyl), $OCF_3$, C(=O)H, C(=O)($C_{1-4}$alkyl), $CO_2H$, $CO_2$($C_{1-4}$alkyl), $NHCO_2$($C_{1-4}$alkyl), S($C_{1-4}$alkyl), $NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$. The term "cycloalkyl" also includes such rings having a second ring fused thereto (e.g., including benzo, heterocyclo, or heteroaryl rings) or having a carbon-carbon bridge of 3 to 4 carbon atoms.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "heteroatoms" shall include oxygen, sulfur and nitrogen.

The term "aryl" refers to phenyl, biphenyl, fluorenyl, 1-naphthyl and 2-naphthyl. The term "aryl" includes such rings having 0, 1, 2 or 3 substituents selected from ($C_{1-4}$alkyl, ($C_{2-4}$)alkenyl, halogen, hydroxy, cyano, nitro, $CF_3$, O($C_{1-4}$alkyl), $OCF_3$, C(=O)H, C(=O)($C_{1-4}$alkyl), $CO_2H$, $CO_2$($C_{1-4}$alkyl), $NHCO_2$($C_{1-4}$alkyl), S($C_{1-4}$alkyl), $NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$.

The terms "heterocyclo" or "heterocyclic" refers to substituted and unsubstituted non-aromatic (which may be partially or fully saturated) 3- to 15-membered rings having 1 to 4 heteroatoms. Such rings can be 3- to 7-membered monocyclic groups, 7- to 11-membered bicyclic groups, and 10- to 15-membered tricyclic groups. Each ring of the heterocyclo group containing a heteroatom can contain one or two oxygen or sulfur atoms and/or from 1 to 4 nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain 0, 1, 2 or 3 substituents selected from ($C_{1-4}$)alkyl, ($C_{2-4}$)alkenyl, halogen, hydroxy, cyano, nitro, $CF_3$, O($C_{1-4}$alkyl), $OCF_3$, C(=O)H, C(=O)($C_{1-4}$alkyl), $CO_2H$, $CO_2$($C_{1-4}$alkyl), $NHCO_2$($C_{1-4}$alkyl), S($C_{1-4}$alkyl), $NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, quinuclidinyl, tetrahydro-1,1-dioxothienyl and the like.

The term "heteroaryl" refers to substituted and unsubstituted aromatic 3- to 14-membered rings having 1 to 4 heteroatoms selected from O, S, or N in at least one of the rings. Said rings can be 5- or 6-membered monocyclic groups, 9- or 10-membered bicyclic groups, and 11- to 14-membered tricyclic groups. Each ring of the heteroaryl group containing a heteroatom can contain one or two oxygen or sulfur atoms and/or from 1 to 4 nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain 0, 1, 2 or 3 substituents selected from $(C_{1-4})$alkyl, $(C_{2-4})$alkenyl, halogen, hydroxy, cyano, nitro, $CF_3$, $O(C_{1-4}$alkyl), $OCF_3$, $C(=O)H$, $C(=O)(C_{1-4}$alkyl), $CO_2H$, $CO_2(C_{1-4}$alkyl), $NHCO_2(C_{1-4}$alkyl), $S(C_{1-4}$alkyl), $NH_2$, $NH(C_{1-4}$alkyl), $N(C_{1-4}$alkyl)$_2$, $N(C_{1-4}$alkyl)$_3^+$, $SO_2(C_{1-4}$alkyl), $C(=O)(C_{1-4}$alkylene)$NH_2$, $C(=O)(C_{1-4}$alkylene)NH(alkyl), and/or $C(=O)(C_{1-4}$alkylene)$N(C_{1-4}$alkyl)$_2$.

Exemplary heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like. Particular heteroaryl groups include, for example, 6-substituted quinazolin-4-yl and 6-trifluoromethyl-quinazolin-4-yl.

Where a group is optionally substituted, it shall include substituted and unsubstituted groups.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, $C=N$ double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of compounds disclosed herein may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Young, S. D. et al., *Antimicrobial Agents and Chemotherapy,* 2602-2605 (1995).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, benzene sulfonic, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit both CCR-2 and CCR-5 or effective to treat or prevent disorders as discussed herein.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

The names used herein to designate a specific form, e.g., "N-1" or "P-1", should not be considered limiting with respect to any other substance possessing similar or identical physical and chemical characteristics, but rather it should be understood that these designations are mere identifiers that should be interpreted according to the characterization information also presented herein.

The present invention provides crystalline forms of the free base of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide as a novel material, in particular, in a pharmaceutically acceptable form. In certain preferred embodiments, crystalline forms of the free base are in substantially pure form. Preferred embodiments of the free base are disclosed in the examples as the N-1 form. Additionally, it is believed that the free base may exist as the P-1 form and/or a combination of the N-1 and P-1 forms.

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further contains molecules of a solvent or solvents incorporated into the crystalline structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein "amorphous" refers to a solid form of a molecule, atom, and/or ions that is not crystalline. An amorphous solid does not display a definitive x-ray diffraction pattern.

As used herein, "substantially pure," when used in reference to a crystalline form, means a compound having a purity greater than 90 weight %, including greater than 90, 91, 92, 93, 94, 95, 96, 97, 98 and 99 weight %, and also including equal to about 100 weight % of Compound I, based on the weight of the compound. The remaining material comprises other form(s) of the compound, and/or reaction impurities and/or processing impurities arising from its preparation. For example, a crystalline form of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, free base or salt, may be deemed substantially pure in that it has a purity greater than 90 weight %, as measured by means that are at this time known and generally accepted in the art, where the remaining less than 10 weight % of material comprises other form(s) of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, free base or salt, and/or reaction impurities and/or processing impurities.

Samples of the crystalline forms may be provided with substantially pure phase homogeneity, indicating the presence of a dominant amount of a single crystalline form and optionally minor amounts of one or more other crystalline forms. The presence of more than one crystalline form in a sample may be determined by techniques such as powder x-ray diffraction (PXRD) or solid state nuclear magnetic resonance spectroscopy (SSNMR). For example, the presence of extra peaks in the comparison of an experimentally measured PXRD pattern with a simulated PXRD pattern may indicate more than one crystalline form in the sample. The simulated PXRD may be calculated from single crystal x-ray data. See Smith, D. K., "A FORTRAN Program for Calculating X-Ray Powder Diffraction Patterns," Lawrence Radiation Laboratory, Livermore, Calif., UCRL-7196 (April 1963).

Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture.

The forms may be characterized and distinguished using single crystal x-ray diffraction, which is based on unit cell measurements of a single crystal of a form at a fixed analytical temperature. A detailed description of unit cells is provided in Stout et al., Chapter 3, *X-Ray Structure Determination: A Practical Guide*, Macmillan Co., New York (1968). Alternatively, the unique arrangement of atoms in spatial relation within the crystalline lattice may be characterized according to the observed fractional atomic coordinates. Another means of characterizing the crystalline structure is by powder x-ray diffraction analysis in which the experimental or observed diffraction profile is compared to a simulated profile representing pure powder material, both run at the same analytical temperature, and measurements for the subject form characterized as a series of 2θ values.

Other means of characterizing the form may be used, such as solid state nuclear magnetic resonance (SSNMR), differential scanning calorimetry and thermogravimetric analysis. These parameters may also be used in combination to characterize the subject form.

The term "negligible weight loss," as employed herein, as characterized by TGA indicates the presence of a neat (non-solvated) crystal form.

In one embodiment of the invention, a crystalline form of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, free base or salt, is provided in substantially pure form. This crystalline form may be employed in pharmaceutical compositions which may optionally include one or more other components selected, for example, from the group consisting of excipients, carriers, and one of other active pharmaceutical ingredients or active chemical entities of different molecular structures.

Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

In another embodiment, a composition is provided consisting essentially of the crystalline forms of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, free base or salt. The composition of this embodiment may comprise at least 90 weight % of the form, based on its weight in the composition.

The presence of reaction impurities and/or processing impurities may be determined by analytical techniques known in the art, such as, for example, chromatography, nuclear magnetic resonance spectroscopy, mass spectrometry or infrared spectroscopy.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Byrn, S. R. et al., *Solid-State Chemistry of Drugs*, 2nd Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed; for example, the compound may be solubilized into a first solvent to afford a solution, followed by the addition of an antisolvent to decrease the solubility of the compound in the solution and to afford the formation of crystals. An "antisolvent" is a solvent in which the compound has low solubility. Suitable solvents for preparing crystals include polar and nonpolar solvents.

In one method to prepare crystals, N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, free base or salt, is suspended and/or stirred in a suitable solvent to afford a slurry, which may be heated to promote dissolution. The term "slurry," as used herein, means a saturated solution, which may also contain an additional amount of the solid to afford a heterogeneous mixture at a given temperature. Suitable solvents in this regard include, for example, polar aprotic solvents and polar protic solvents, and mixtures of two or more of these, as disclosed herein.

Seed crystals may be added to any crystallization mixture to promote crystallization. As will be clear to the skilled artisan, seeding is used as a means of controlling growth of a particular crystalline form or as a means of controlling the particle size distribution of the crystalline product. Accordingly, calculation of the amount of seeds needed depends on the size of the seed available and the desired size of an average product particle as described, for example, in Mullin, J. W. et al., "Programmed cooling of batch crystallizers," *Chemical Engineering Science*, 26:369-377 (1971). In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal form (i.e., change to amorphous or to another polymorph).

A cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as SSNMR, DSC, PXRD, or the like, to assure formation of the preferred crystalline form of the product. The resulting crystalline form is typically produced in an amount of greater than about 70 weight % isolated yield, but preferably greater than 90 weight % based on the weight of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, free base or salt, originally employed in the crystallization procedure. The product may be co-milled or passed through a mesh screen to de-lump the product, if necessary.

Crystalline forms may be prepared directly from the reaction medium of the final process step for preparing N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, free base or salt. This may be achieved, for example, by employing in the final process step a solvent or mixture of solvents from which the compound may be crystallized. Alternatively, crystalline forms may be obtained by distillation or solvent addition techniques. Suitable solvents for this purpose include any of those solvents described herein, including protic polar solvents, such as alcohols, and aprotic polar solvents, such as ketones.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like. By way of general guidance, the reaction solution may be distilled to about 1/10 the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

It may be preferable to add solvents directly to the reaction vessel without distilling the reaction mixture. Preferred solvents for this purpose are those which may ultimately participate in the crystalline lattice, as discussed above in connection with solvent exchange. Although the final concentration may vary depending on desired purity, recovery and the like, the final concentration of the free base in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The various forms described herein may be distinguishable from one another through the use of various analytical techniques known to one of ordinary skill in the art. Such techniques include, but are not limited to, powder x-ray diffraction (PXRD), differential scanning calorimetry (DSC) and/or thermogravimetric analysis (TGA). Alternatively, the forms may be characterized and distinguished using single crystal x-ray diffraction, which is based on unit cell measurements of a single crystal of a given form at a fixed analytical temperature. A detailed description of unit cells is provided in Stout et al., Chapter 3, *X-Ray Structure Determination: A Practical Guide*, Macmillan Co., New York (1968). Specifically, the unique arrangement of atoms in spatial relation within the crystalline lattice may be characterized according to the observed fractional atomic coordinates. Another means of characterizing the crystalline structure is by powder x-ray diffraction analysis in which the observed diffraction profile is compared to a simulated profile generated from single crystal structure data. Powder x-ray diffraction measurements for the subject form are characterized as a series of 2θ values (usually four or more).

Other means of characterizing the form may be used, such as solid state nuclear magnetic resonance (SSNMR) spectroscopy, differential scanning calorimetry (DSC), thermography and gross examination of the crystalline or amorphous morphology. These parameters may also be used in combination to characterize the subject form.

One of ordinary skill in the art will appreciate that an x-ray diffraction pattern may be obtained with a measurement error that is dependent upon the measurement conditions employed. In particular, it is generally known that intensities in an x-ray diffraction pattern may fluctuate depending upon measurement conditions employed and the shape or morphology of the crystal. It should be further understood that relative intensities may also vary depending upon experimental conditions and, accordingly, the exact order of intensity should not be taken into account. Additionally, a measurement error of diffraction angle for a conventional x-ray diffraction pattern is typically about 0.2° 2θ values or less, preferably about 0.1° 2θ values (as discussed hereinafter), and such degree of measurement error should be taken into account as pertaining to the aforementioned diffraction angles. Consequently, it is to be understood that the crystal forms of the instant invention are not limited to the crystal forms that provide x-ray diffraction patterns completely identical to the x-ray diffraction patterns depicted in the accompanying Figures disclosed herein. Any crystal forms that provide x-ray diffraction patterns substantially identical to those disclosed in the accompanying Figures fall within the scope of the present invention. The ability to ascertain substantial identities of x-ray diffraction patterns is within the purview of one of ordinary skill in the art.

Synthesis

Scheme 1: Preparation of hydrazone I-dd

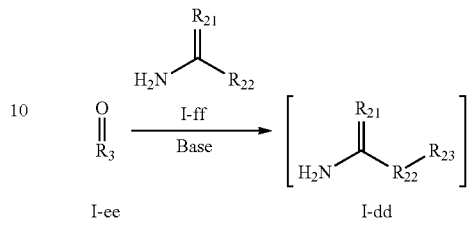

A carbazide of formula I-ff, such as semicarbazide hydrochloride, was condensed with a compound of formula I-ee, such as pivaloyl acetonitrile, in a solvent, for example, ethanol, 2-propanol, 1-propanol and methanol, preferably ethanol, in the presence of a base, for example, sodium acetate, potassium acetate, triethylamine and N—N-diisopropyl-N-ethyl amine, preferably sodium acetate, at a temperature in the range of 20-60° C., preferably, in the range of 25-55° C., to provide the hydrazone compound of formula I-dd, wherein $R_{21}$ is =O; $R_{22}$ is —NH—NH$_2$; and $R_{23}$ is cyanoalkyl; or $R_{22}$ and $R_{23}$ may be taken together to form a 5- to 8-membered ring, wherein the ring may be optionally substituted with one or more substituents selected from amino, alkyl, aryl, or heteroaryl and may optionally contain 1, 2, 3 or 4 heteroatoms independently selected from the group consisting of N, S, or O.

Scheme 2: Preparation of hydrazone of Formula I-cc

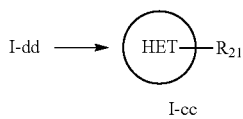

A hydrazone compound of formula I-dd, such as

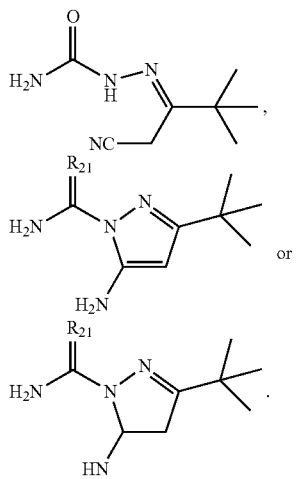

was reacted with an orthoformate, for example, trimethylorthoformate, triethylorthoformate, and tripropylorthoformate, preferably, trimethylorthoformate, orthoformate in the presence of an acid, for example, acetic acid, trifluoroacetic acid, hydrochloric acid and methanesulfonic acid, preferably acetic acid, at elevated temperature, such as 40-90° C., preferably, 40-75° C., to yield the hydrazone compound of formula I-cc, wherein $R_{21}$=O and $R_{22}$ and $R_{23}$ are as set forth above.

Scheme 3: Conversion of Compound I-cc

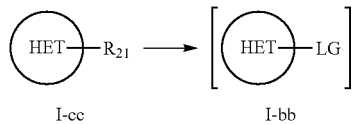

I-cc          I-bb

A hydrazone compound of formula I-cc is converted to a compound of Formula I-bb, wherein LG is —$OR_{16}$, wherein $R_{16}$ is $C_{1-6}$alkyl, phenyl, a 5- to 7-membered heteroaryl having one or more atoms selected from N, S, or O, or a 3- to 7-membered cycloalkyl, all of which are optionally substituted with 1 to 3 groups selected from halogen, $CF_3$ or $C_{1-6}$alkyl, by reacting the hydrazone compound of formula I-cc, for example, 7-tert-butyl-3H-pyrazolo[1,5-a][1,3,5]triazin-4-one, with an acylating agent, a nucleophile, such as dimethyl 4-aminopyridine (DMAP), and/or a tertiary amine base, in a solvent, for example, acetonitrile, dichloromethane and neat phosphorus oxychloride, followed by interception with either (i) an alcohol in the presence of a second tertiary amine base or (ii) an alkoxide to form the compound of formula I-bb. Examples of acylating agents that may be used are phosphorus oxychloride ($POCl_3$), oxalyl chloride, thionyl chloride and phosgene. A preferred acylating agent is $POCl_3$. Triethylamine, N—N-diisopropyl-N-ethyl amine (DIEA), tri-n-propylamine, N-methyl morpholine and 1,4-diazabicyclo[2.2.2]octane (DABCO) are examples of tertiary amine bases that may be used in the conversion. A preferred tertiary amine base is DIEA. Generally, the amount of nucleophile used in the reaction is 2.0 to 4.0, preferably, 3.0, equivalents. Examples of alcohols or alkoxides that may be used in the conversion are phenol, pentafluorophenol, methanol, ethanol, sodium methoxide and sodium phenolate with phenol being the preferred alcohol. Generally, the reaction and interception may be carried out at a temperature in the range of ambient temperature to 70° C.

Scheme 4: Preparation of a compound of formula I, or a salt thereof

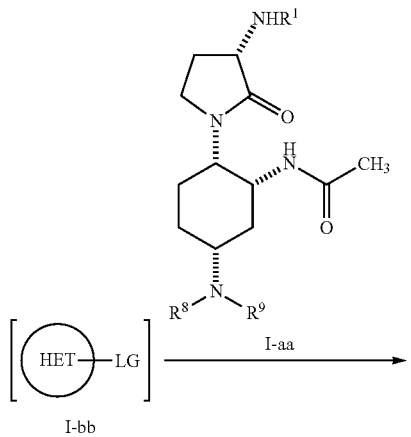

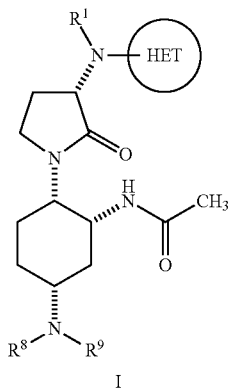

I

A compound of formula I-bb, for example,

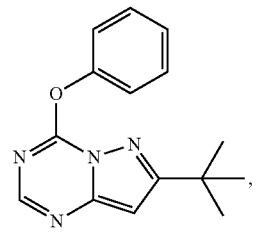 [SMILES: CC(C)(C)c1cc2ncnc(Oc3ccccc3)n2n1]

is coupled with a compound of formula I-aa, prepared in a similar manner as described in WO 2008/014381 A1, wherein: $R_1$ is independently hydrogen or an amine-protecting group selected from a carbobenzyloxy (Cbz) group, a tert-butyloxycarbonyl (BOC), a fluorenylmethyloxycarbonyl (FMOC) group, a benzyl (Bn) group, and a p-methoxybenzyl (PMB) group, preferably hydrogen; $R_8$ and $R_9$ are independently hydrogen or $C_{1-6}$alkyl; $R_{21}$ is =O; HET is an optionally substituted 3- to 14-membered heterocyclo or heteroaryl bicyclic ring having at least one nitrogen heteroatom, preferably two to four total heteroatoms, especially four nitrogen atoms; and LG is —$OR_{16}$, wherein $R_{16}$ is $C_{1-6}$ alkyl, phenyl, a 5- to 7-membered heteroaryl having one or more atoms selected from N, S, or O, or a 3- to 7-membered cycloalkyl, all of which are optionally substituted with 1 to 3 groups selected from halogen, $CF_3$ or $C_{1-6}$alkyl, to obtain the corresponding compound of formula I, for example, N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, or a salt thereof. Coupling may be performed by coupling methods commonly known in art, or, alternatively, via an acidic work-up followed by the addition of a base. Examples of acids that may be used in the acidic work-up are citric acid, tartaric acid, glycolic acid, and hydrochloric acid. Examples of bases that may be added are $K_2HPO_4$, $Na_2HPO_4$, $NaHCO_3$ and $KHCO_3$.

Specifically, N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide may be prepared according to the following scheme:

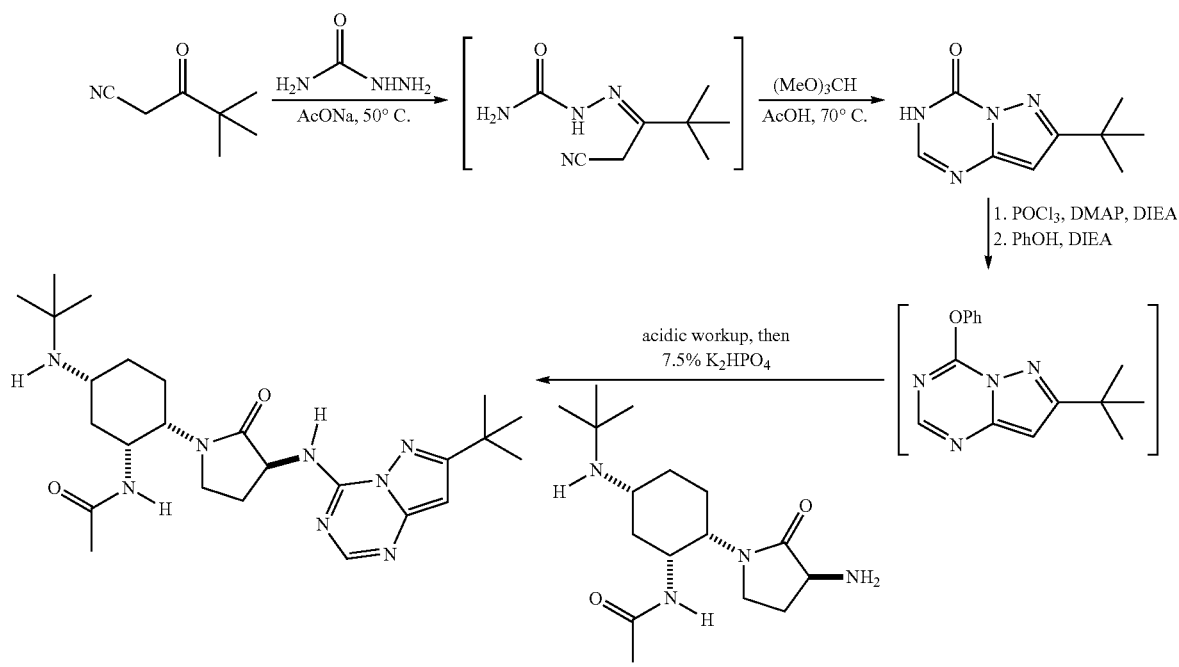

For the process of this invention, starting materials are commercially available or can be readily prepared by one or ordinary skill in the art. Solvents, temperatures, pressures, starting materials having the desired groups, and other reaction conditions, may be readily selected as appropriate by one of ordinary skill in the art. The process can be scaled up in order to prepare larger quantities of the compound of formula I, such as in a commercial production facility.

EXAMPLES

The following Examples illustrate embodiments of the inventive compounds and starting materials, and are not intended to limit the scope of the claims.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

LC/MS measurements were obtained using a Shimadzu HPLC/Waters ZQ single quadropole mass spectrometer hybrid system. Data for the peak of interest are reported from positive-mode electrospray ionization. NMR (nuclear magnetic resonance) spectra were typically obtained on Bruker or JEOL 400 MHz and 600 MHz instruments in the indicated solvents. All chemical shifts are reported in ppm from tetramethylsilane with the solvent resonance as the internal standard. $^1$H NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

One of skill in the art will recognize the standard abbreviations utilized herein. For ease of reference, the abbreviations include, but are not necessarily limited to: Hg=mercury; sat.=saturated, HPLC=high-performance liquid chromatography, AP=area percent, KF=Karl-Fischer, RT=room temperature (unless specified otherwise RT is a temperature of about 22° C.), mmol=millimoles, HRMS=high-resolution mass spectroscopy, ° C.=degrees Celsius, kg—kilogram or kilograms, g=gram or grams, mg=milligram or milligrams, L=liter or liters, mL (or ml)=milliliter or milliliters, h or hr=hour or hours, M=molar, N=normal, min=minute or minutes, MHz=megahertz, v/v=volume to volume ratio, % w/w=weight/weight percent, wt %=weight percent, nm=nanometer or nanometers, LOD=loss of drying.

"α", "β", "R" and "S" are stereochemical designations familiar to those skilled in the art.

Example 1

N-((1R,2S,5R)-5-(tert-Butylamino)-2-((S)-3-(7-tert-butylpyrazolo[1,5-a][1,3,5]triazin-4-ylamino)-2-oxopyrrolidin-1-yl)cyclohexyl)acetamide

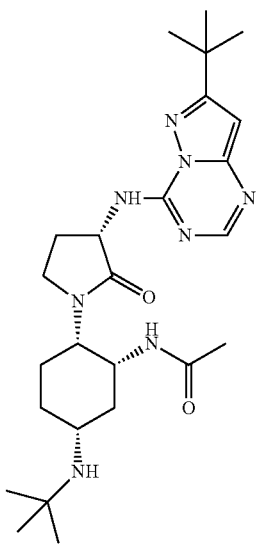 [SMILES: CC(=O)N[C@@H]1C[C@H](NC(C)(C)C)CC[C@@H]1N1CC[C@H](Nc2ncnc3cc(C(C)(C)C)nn23)C1=O]

Example 1, Step 1

To a 3 L round-bottom flask was added semicarbazide hydrochloride (100.0 g, 0.89 moles), pivaloyl acetonitrile (112.2 g, 0.89 moles) and ethanol (1 L) at 22-25° C. Upon completion of addition, the reaction mixture was cooled to 12-15° C. and anhydrous sodium acetate (73.5 g, 0.89 moles) was added. The addition of the anhydrous sodium acetate was endothermic thereby raising the temperature to 22-25° C. The reaction mixture was maintained at 22-25° C. and stirred for 60-90 minutes. After this time, the reaction mixture was analyzed by HPLC, which indicated that the formation of the hydrazone intermediate was complete.

Example 1, Step 2

The reaction mixture was then heated to 68-72° C. and trimethylorthoformate (475.7 g, 4.48 moles) was added during a 5-10 minute period. The reaction mixture was allowed to cool to 40-45° C. and then acetic acid (53.8 g, 0.89 moles) was added during a 15-20 minute period. Upon completion of addition, the temperature was raised to 70±2° C. during a 20-25 min period. Once at the prescribed temperature, the reaction mixture was stirred for 18-20 hr. At the conclusion of this period, the reaction mixture was analyzed by HPLC, which indicated that the formation of the pyrazolo[1,5-a][1,3,5]triazine was complete.

Example 1, Step 3

The pyrazolo[1,5-a][1,3,5]triazine from Example 1, Step 2, was concentrated at 50-55° C. under reduced pressure (~5-10 mm Hg) to yield a residue. Tetrahydrofuran (THF, 2 L) and acetone (2 L) were added to the residue, and the resulting mixture was stirred at 50-55° C. for 90 minutes. After this time, the reaction mixture was filtered through Buckner funnel to remove the resultant sodium chloride (NaCl) and sodium acetate (NaOAc) precipitates. The resulting filtrate was concentrated to dryness at 50-55° C. under reduced pressure (~400-450 mm Hg) to yield a residue. The residue was taken up in 2-methylorthoformate (2-methyl THF, 450 mL) and the resulting mixture was stirred at 22-25° C. for two (2) hours. At the conclusion of this period, the reaction mixture was filtered and then spray washed with 2-methyl THF (100 mL), followed by tert-butyl methyl ether (MTBE, 200 mL). The resulting product was dried at 45-50° C. reduced pressure (~400-450 mm Hg) to provide 7-tert-butylpyrazolo[1,5-a][1,3,5]triazin-4(3H)-one (107.0 g, 62.1% w/w, HPLC purity: 99.2 AP at 220 nm). Steps 1 to 3 were repeated on a larger scale to produce kilogram quantities of 7-tert-butylpyrazolo[1,5-a][1,3,5]triazin-4(3H)-one.

Example 1, Step 4

To a glass lined reactor was added 7-tert-butylpyrazolo[1,5-a][1,3,5]triazin-4(3H)-one (1.0 kg, 5.2 moles), dimethyl 4-aminopyridine (1.27 kg, 10.4 moles), acetonitrile (10 L), and diisopropylethylamine (0.672 kg, 5.2 mole). The resulting slurry was stirred at ambient temperature under a nitrogen atmosphere for a period of no less than 15 minutes until a clear solution was formed. The clear solution was slowly added to a second glass lined reactor containing acetonitrile (6.0 L) and phosphorus oxychloride ($POCl_3$, 0.822 kg, 5.3 moles). Upon completion of addition, the resulting mixture was stirred at below 35° C. for 2 hours. At the conclusion of this period, the reaction was analyzed by HPLC, which indicated that the reaction was complete. Phenol (0.64 kg, 6.8 mole) and diisopropylethylamine (0.87 kg) were added and the resulting reaction mixture was stirred at ambient temperature for no less than 1 hr. After this time, the reaction mixture was analyzed by HPLC, which indicated that the reaction was completed. 2-Methyl-THF (20 L), followed by water (10 L) were added to the reaction mixture. The organic and aqueous phases were separated and the aqueous phase was discarded. The organic phase was washed with a citric acid-brine solution (5 wt %, 10 L), and the resulting organic and aqueous phases were separated and the aqueous phase was discarded again. The above citric acid-brine solution wash was repeated two more times. Upon completion of the citric acid-brine solution washes, a potassium phosphoric base solution ($K_2HPO_4$, 7.5 wt %, 10 L) was added. The organic and aqueous phases were separated and the aqueous phase was discarded. The above $K_2HPO_4$ solution wash was repeated one more time until pH ~8.

Example 1, Step 5

N-[2-(3-Amino-2-oxo-pyrrolidin-1-yl)-5-tert-butylamino-cyclohexyl]-acetamide (prepared in a similar manner as described in U.S. Publication No. 2008/0027083 A1, 1.05 kg) was added to the basic organic phase from Example 1, Step 4. Upon completion of addition, the reaction mixture was stirred at ambient temperature for 16 hr. At the conclusion of this period, the reaction mixture was analyzed by HPLC, which indicated the reaction was complete. Water (20 L) followed by acetic acid (HOAc, 0.406 kg) were added to the reaction mixture, and the resulting organic and aqueous layers were separated. The aqueous layer was extracted with 2-methyl THF (10 L). The organic layers were combined and HOAc (0.406 kg) was added. The resulting mixture was washed with water (10 L) and the resulting organic and aqueous layers were separated. This aqueous layer was extracted again with 2-methyl-THF (10 L). The aqueous layers were combined again and dichloromethane (DCM, 15 L) was added. Sodium hydroxide (NaOH, 10 N, 1.04 L) was added to adjust the pH to ~13.0. Upon completion of addition, the organic and aqueous layers were separated again and the product-rich DCM layer was set aside. The aqueous layer was extracted with additional dichloromethane (10 L). The DCM rich organic layers were combined and washed with water (10 L). The resulting product rich DCM solution was concentrated in vacuo to a minimum volume. Ethyl acetate (EtOAc) was added and the residual DCM and water were continuously distilled off to yield a slurry (final volume ~5 L). MTBE (15 L) was added and the resulting slurry was stirred for no less than 1 hr. After this time, the slurry was filter and the wet filter cake was washed with additional MTBE (5 L). The wet cake was dried at 55° C. in vacuo until LOD≤0.5 wt % to afford the amorphous free base of Example 1 (0.9 kg, 55 M % yield, HPLC purity: 99.5 AP). $^1$H NMR (600.13 MHz, DMSO-$d_6$) δ 1.04 (s, 9H), 1.34 (s, 9H), 1.58 (m, 3H), 1.64 (m, 2H), 1.81 (s, 3H), 2.05 (m, 1H), 2.12 (m, 1H), 2.36 (m, 1H), 2.93 (br s, 1H), 3.48 (m, 2H), 3.84 (m, 1H), 4.26 (br s, 1H), 4.86 (t, J=8.9 Hz, 1H), 6.39 (s, 1H), 8.07 (s, 1H), 8.94 (br s, 1H); $^{13}$C NMR (125.8 MHz, DMSO-$d_6$) δ 21.3, 23.3, 25.9, 29.3, 30.0, 32.2, 32.6, 35.5, 43.1, 46.5, 47.7, 50.7, 51.7, 52.5, 92.3, 148.7, 148.8, 152.9, 167.3, 168.5, 171.2; HRMS calcd for $C_{25}H_{40}N_8O_2$ (M+1) 485.3274. found 485.3343.

Example 2

Tritium-labeled N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide

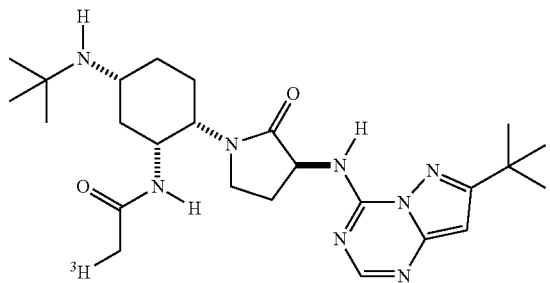 [SMILES: [3H]CC(=O)N[C@@H]1C[C@H](NC(C)(C)C)CC[C@@H]1N1CC[C@H](Nc2ncnc3cc(C(C)(C)C)nn23)C1=O]

Example 3

Deuterium-labeled N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide

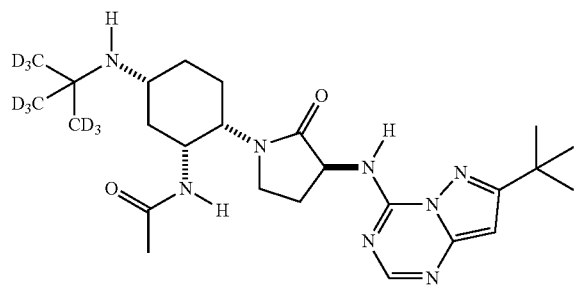 [SMILES: [2H]C([2H])([2H])C(N[C@@H]1CC[C@H](N2CC[C@H](Nc3ncnc4cc(C(C)(C)C)nn34)C2=O)[C@H](NC(C)=O)C1)(C([2H])([2H])[2H])C([2H])([2H])[2H]]

Example 4

Carbon-14 labeled N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide

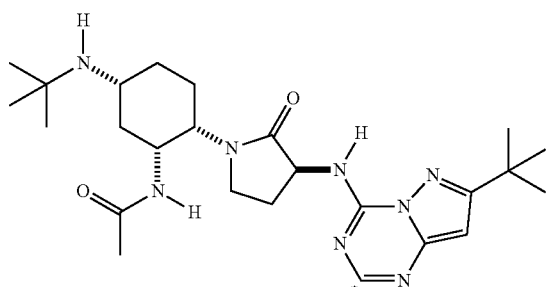

* = Position of $^{14}C$ label

Example 5

N-1 Crystal Form of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide A free base crystal form of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl)acetamide, including salt forms, and solvates thereof, was prepared and characterized as described below.

Procedures for Characterizing the Forms

Single Crystal Data

Data were collected on a Bruker-Nonius (Bruker AXS, Inc., 5465 East Cheryl Parkway Madison, Wis. 53711 USA) CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package (Otwinowski, Z. et al. in *Macromolecular Crystallography*, Carter, W. C., Jr. et al., eds., Academic, NY, publ., Vol. 276, pp. 307-326 (1997)) in the Collect program suite. (Collect Data collection and processing user interface: Collect: Data collection software, R. Hooft, Nonius B. V., 1998.) Alternately, single crystal data were collected on a Bruker-AXS APEX2 CCD system using Cu Kα radiation (λ=1.5418 Å). Indexing and processing of the measured intensity data were carried out with the APEX2 software package/program suite (APEX2 Data collection and processing user interface: APEX2 User Manual, v1.27; Bruker AXS, Inc., 5465 East Cheryl Parkway Madison, Wis. 53711 USA).

When indicated, crystals were cooled in the cold stream of an Oxford cryo system (Oxford Cryosystems Cryostream cooler: Cosier, J. et al., *J. Appl. Cryst.*, 19:105 (1986)) during data collection.

The structures were solved by direct methods and refined on the basis of observed reflections using either the SDP (SDP, Structure Determination Package, Enraf-Nonius, Bohemia N.Y. 11716. Scattering factors, including f' and f", in the SDP software were taken from the *International Tables for Crystallography*, Kynoch Press, Birmingham, England, Vol. IV, Tables 2.2A and 2.3.1 (1974)) software package with minor local modifications or the crystallographic packages MAXUS (maXus solution and refinement software suite: Mackay, S. et al., maXus: a computer program for the solution and refinement of crystal structures from diffraction data or SHELXTL4. The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w = [\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

X-Ray Powder Diffraction Data (PXRD)

PXRD data were obtained using a Bruker C2 GADDS. The radiation was Cu Kα (40 KV, 50 mA). The sample-detector distance was 15 cm. Powder samples were placed in sealed glass capillaries of 1 mm or less in diameter; the capillary was rotated during data collection. Data were collected for 3≤2θ≤35° with a sample exposure time of at least 2000 seconds. The resulting two-dimensional diffraction arcs were integrated to create a traditional 1-dimensional PXRD pattern with a step size of 0.02 degrees 2θ in the range of 3 to 35 degrees 2θ. About 200 mg were packed into a Philips powder x-ray diffraction (PXRD) sample holder. The sample was transferred to a Philips MPD unit (45 KV, 40 mA, Cu Kα). Data were collected at room temperature in the 2 to 32 2-theta range (continuous scanning mode, scanning rate 0.03 degrees/sec., auto divergence and anti scatter slits, receiving slit: 0.2 mm, sample spinner: ON)

Differential Scanning Calorimetry (DSC)

DSC experiments were performed in a TA INSTRUMENTS® model Q1000 or 2920. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

Thermal Gravimetric Analysis (TGA)

TGA experiments were performed in a TA INSTRUMENTS® model Q500 or 2950. The sample (about 10-30 mg) was placed in a previously tared platinum pan previously tared. The weight of the sample was measured accurately and recorded to a thousandth of a milligram by the instrument. The furnace was purged with nitrogen gas at 100 mL/min. Data were collected between room temperature and 300° C. at 10° C./min heating rate.

Preparation and Analysis of the Forms

The unit cell data and other properties for the example are presented in Table 1. The unit cell parameters were obtained from single crystal x-ray crystallographic analysis. A detailed account of unit cells can be found in Chapter 3 of Stout et al., *X-Ray Structure Determination: a Practical Guide*, Macmillan (1968).

Finally, FIG. 1 presents the XRPD pattern for Example 5. FIGS. 2 and 3 disclose the DSC and TGA analysis, respectively, of Example 5.

Form Preparation, XRD, DSC and TGA Characterization

Example 5

N-1 Form, Free Base

N-((1R,2S,5R)-5-(tert-Butylamino)-2-((S)-3-(7-tert-butylpyrazolo[1,5-a][1,3,5]triazin-4-ylamino)-2-oxopyrrolidin-1-yl)cyclohexyl)acetamide, form N-1, was crystallized from ethyl acetate and MTBE. Form N-1, is a neat (no molecules of water or solvent) form of N-((1R,2S,5R)-5-(tert-butylamino)-2-((S)-3-(7-tert-butylpyrazolo[1,5-a][1,3,5]triazin-4-ylamino)-2-oxopyrrolidin-1-yl)cyclohexyl) acetamide. Form N-1 was characterized by a XRD pattern which matches the simulated pattern generated from the single crystal structure data. Form N-1 was characterized by a DSC thermogram having a melt/decomposition endotherm with an onset typically at ca. 205° C. Form N-1 was characterized by a TGA thermal curve having a weight loss at up to ca. 210° C.

TABLE 1

| Unit Cell Parameters | |
|---|---|
| Compound | Exp 5 |
| Structure | Base |
| Form | N-1 |
| T | −70 |
| a(Å) | 7.3085(6) |
| b(Å) | 16.257(1) |
| c(Å) | 22.688(2) |
| α° | 90 |
| β° | 90 |
| γ° | 90 |
| V(Å$^3$) | 2695.4(4) |
| Z' | 1 |
| Vm | 673 |
| Sg | P2$_1$2$_1$2$_1$ |
| Dcalc | 1.194 |

The variables used in Table 1 are defined below:
T=temperature in Centigrade for the crystallographic data (RT is room temperature which is about +22° C.)
V=volume of unit cell
Z'=number of drug molecules per asymmetric unit
Vm=V(unit cell)/(Z drug molecules per cell)
sg=space group
dcalc=calculated crystal density Comparative Pharmacological Characteristics Assays and data comparing the pharmacological characteristics of Example 1 and compounds found in WO 2005/021500 A1, WO 2008/014381 A1 and WO 2008/014360 A1 are presented below.

Human Peripheral Blood Mononuclear Cell Binding

See also: Yoshimura et al., *J. Immunol.*, 145:292 (1990). The human CCR-2 binding assay was established with human peripheral blood mononuclear cells (hPBMCs) using $^{125}$I-human MCP-1 as the tracer ligand. hPBMCs were isolated from human leukopak (Biological Specialty Inc.) using a standard protocol with Ficoll-Hypaque (Mediatech CELL-GRO®). Isolated hPBMCs were washed and diluted to 1×10$^7$/ml in binding buffer (RPMI-1640, 0.1% BSA, 20 mM Hepes, pH 7.4). $^{125}$I-MCP-1 (NEN/Perkin Elmer) was diluted to 0.45 nM in binding buffer. The compound was diluted in binding buffer at 3-fold the final concentrations used in the binding assay. The binding assay was performed using a 96-well filter plate (Millipore). Total $^{125}$I-MCP-1 binding was assessed as follows: to each reaction of a total volume of 150 µl were added 5×10$^5$ cells, 0.15 nM $^{125}$I-MCP-1, and compound such that the final concentration ranged from 0 to 100 nM. The plate was incubated at room temperature for 30 minutes followed by three washes with RPMI-1640, 0.1% BSA, 0.4 M NaCl, 20 mM Hepes, pH 7.4 using a vacuum manifold filtration (Millipore). After washing, the plate was air-dried for 60 minutes at room temperature. This was followed by adding 25 µl of Microscint 20 into each well. The plate was sealed and counted on the Trilux for 1 minute. Non-specific binding was determined in the presence of 300 nM cold MCP-1 (PeproTech Inc.). Specific $^{125}$I-MCP-1 was calculated as the difference between total and non-specific binding. All conditions were tested in duplicate. The IC50 is defined as the concentration of competing compound required to reduce specific binding by 50%.

The procedure used for T cell CCR-5 binding assay was similar to those for hPBMC CCR-2 binding assay except that human peripheral T cells was used as a source of CCR-5 (see below) and $^{125}$I-MIP-1β as a tracer (Amersham).

Isolation of Peripheral T Cells

A recent report indicates that CCR-5 expression on T cells varies considerably among individuals (Desmetz, C. et al., "The strength of the chemotactic response to a CCR-5 binding chemokine is determined by the level of cell surface CCR-5 density", *Immunology*, 119(4):551-561 (2006)). Therefore, blood donors were pre-screened for high T-cell expression of CCR-5. hPBMCs were first isolated from human whole blood by standard protocol with Ficoll-Hypaque. Flow cytometric analysis was then used to measure CCR-5 expression on T cells following staining with anti-CCR-5 antibody plus anti-CD4 antibody or anti-CD8 antibody. Those blood donors in which >5% peripheral T cells (CD4$^+$ and CD8$^+$) express CCR-5 were requested to provide blood again for isolation of PBMCs and, subsequently, of T cells using a standard E-rosetting technique which relies on the unique ability of T cells to bind to sheep red blood cells (RBCs).

CCR-2 Chemotaxis

The human CCR-2 chemotaxis assay was conducted with the human monocytic cell line, THP-1. THP-1 cells were first labeled with the fluorescent dye Calcein-AM in phenol red-free, BSA-free RPMI-1640 (pH 7.4) at 37° C. for 30 minutes with gentle mixing every 15 minutes. The labeled cells were then washed and re-suspended at 1×10$^5$/ml in chemotaxis buffer (phenol red-free RPMI-1640, 0.1% BSA, pH 7.4). The test compound was diluted in chemotaxis buffer such that the final assay concentration ranged from 0.01 nM to 1 µM. The ligand MCP-1 (PeproTech Inc.) was diluted to 20 nM in chemotaxis buffer. To perform the assay, an equal volume of test compound dilutions was mixed with an equal volume of labeled THP-1 cells (Mixture 1), and an equal volume of test compound dilutions was mixed with an equal volume of diluted MCP-1 ligand (Mixture 2). Both mixtures were incubated independently at 37° C. for 10 minutes followed by gentle mixing. MCP-1-induced chemotaxis was then measured in a chemotaxis plate (Becton Dickinson) by placing 50 µl of Mixture 1 in the top chamber and 225 µl of Mixture 2 in the bottom chamber. The plate was covered with a lid and incubated at 37° C. for 30 minutes. 30 minutes later, the plate was read on a CYTOFLUOR®. All conditions were tested in duplicate. For signal to noise determination, 50 µl of labeled THP-1 cells alone (5×10$^4$/well) were placed into the top chamber and 225 µl of ligand MCP-1 alone was placed in the bottom chamber (final concentration of 10 nM). The inhibition achieved by graded concentrations of test compound was calculated as a percentage of the compound-free MCP-1 control. The IC50 is defined as the concentration of test compound required to reach 50% inhibition of cellular chemotaxis.

CCR-5 Chemotaxis

A similar procedure to that set forth above was adopted except that isolated peripheral T cells was used as CCR-5-expressing cells and MIP-1β (50 nM, PeproTech Inc.) was the ligand.

hERG Flux

HEK293 cells stably-expressing hERG channels were grown (37° C., 5% CO$_2$) in Dulbecco's Modified Eagle's Media supplemented with 10% Sigma fetal bovine serum, non-essential amino acids, 2 mM L-glutamine and 500 µg/ml G418, at incubator. Cell dissociation buffer was used to extract the cells from flasks, which were then plated into 384-well CORNING® poly-D-lysine coated black/clear plates at a density of 2×10$^4$ cells per well (20 µl) in 10% serum media, and incubated for 15-24 hours at 37° C. in a 5% CO$_2$ incubator until a confluent monolayer of cells was obtained.

A 2 mM stock of BTC-AM dye (Molecular Probes, Eugene, Oreg.) was prepared in 100% DMSO and then added 1:1 to 10% (w/v) pluronic acid in DMSO on the day of assay. The dye was then diluted in hERG external EP buffer (140 mM NaCl, 4.0 mM KCl, 1.8 mM CaCl$_2$, 1.0 mM MgCl$_2$, 10 mM HEPES, pH 7.3 and 10 mM glucose; all buffer components obtained from Sigma Chemical). This BTC dye mixture (30 µl) was added to the cells and produced a final loading concentration of 2.5 µM. Cells are incubated at 21° C. for 45 minutes.

The test compound was diluted to 10 mM DMSO in 60 µl. The compound was then serially-diluted at a 1:2 ratio in DMSO in columns 1-10 and 11-20 of a 384-well plate. Assay-ready plates were generated by stamping 2.5 µl from the DMSO serially diluted plate, which was prepared on the Velocity 11 BIOCEL®. Aqueous plates were created by adding 48 µl of EP buffer and then were diluted 30-45 minutes before the assay was read on the FLIPR®. After dye loading, aqueous-diluted compound was added to the cells of the three replicate plates (10 µl) yielding a ten point concentration range of 80 µM to 0.156 nM. Final DMSO concentration in the assay is 1%. Assay-ready aqueous plates were prepared and diluted on a CyBio liquid handler.

Cells loaded with dye were read on the FLIPR®384 (Molecular Devices, Sunnyvale, Calif.), which excites the dye using the 488 nm line of an argon laser. Emission was filtered using a 540±30 nm bandpass filter. hERG channels are stimulated to open by the addition of 20 µl/well EP buffer containing 66 mM K$_2$SO$_4$ and 1.3 mM Tl$_2$SO$_4$ (Sigma/Aldrich). For each plate, data were collected every second for a period of 12 seconds, at which time the Tl$^+$-containing stimulus buffer was added. Data collection proceeded every second for 48 seconds, and then continued every three seconds for an additional 2 minutes.

The dynamic range of the assay was determined from blanks and totals wells. The totals wells (columns 21 and 22) define maximal hERG activation for the plate (no test compound present), and the blanks wells (columns 23 and 24) define 100% hERG inhibition. The blanks wells contain 400 nM of either of the standard hERG inhibitors dofetilide (Ficker et al., 1998) or E-4031. Raw data points in each sample well were first corrected for cell/signal variation, negative control (blanks) background, and normalized to the positive controls (totals) using the online FLIPR® software. Test compound concentration response curves for the hERG Tl$^+$ flux data were then fit using Excel Fit (ID Business Solutions Limited, Surrey, UK) with a single-site logistic equation, $Y=A+((B-A)/1+((C/X)\hat{}D)))$ where A=maximal inhibition. Data were analyzed by fitting maximum amplitudes of change in fluorescence for Tl$^+$ flux for a given condition of test compound. Potencies (IC$_{50}$ values) of compound were calculated from the average of triplicate wells.

Sodium Channel, Site 2 Binding Assay

See also: Catterall, W. A. et al. *J. Biol. Chem.*, 256:8922 (1981). The standard binding buffer contained 50 mM HEPES, 50 mM Tris-HCl, pH 7.4, 130 mM choline chloride, 5.4 mM KCl, 0.8 mM MgCl$_2$, 5.5 mM glucose, 40 µg/mL LqT. Binding reactions were initiated by adding synaptosomes (prepared from Wistar rat brain) to the reaction mixture containing 5 nM [$^3$H]-batrachotoxin in a standard binding buffer and the compound to be tested at the desirable concentration. Samples were then mixed and incubated at 37° C. for 60 minutes. The reactions were stopped by adding ice-cold washing buffer containing 50 mM HEPES, 50 mM Tris-HCl, pH 7.4, 1.8 mM CaCl$_2$, 0.8 mM MgCl$_2$ and 1 mg/mL bovine serum albumin. The synaptosomes were immediately collected onto glass fiber filters and washed 3 times with washing buffers. The radioactivity of [$^3$H]-batrachotoxin remaining on the filters was counted using liquid scintillation spectrometers.

Parallel Artificial Membrane Permeability Assay (PAMPA)

The Parallel Artificial Membrane Permeability Assay (PAMPA) consists of a specially formulated lecithin-based lipid combination referred to as the gastrointestinal tract (GIT) lipid. The GIT lipid is used to form a membrane in a sandwich plate assembly similar to that used in the Caco-2 assays. The GIT lipid closely resembles in vivo membrane composition and performance as measured by standard compounds that are known to be passively absorbed in humans. PAMPA is widely used as an in vitro model for permeability screening of discovery compounds. The rate of passage of compounds through the PAMPA membrane is used to determine a permeability coefficient (Pc), which can be related to the in vivo passive permeability of the compound.

The permeability coefficient (Pc) of a particular compound is examined in a pH-dependent setting with apical and basolateral pH of 7.4. All experiments are conducted in triplicate determinations.

The test compound (10 mM stocks in 100% DMSO) was diluted 1:100 in pH 7.4 donor well buffer (pION CAT #110151), providing a 100 μM assay solution in 1% DMSO. Compound diluted in donor well buffer was transferred to a Whatman UNIFILTER® plate and filtered prior to dispensing 200 μl into the donor well of the assay plate (pION CAT #110163). The PAMPA membrane was formed by pipetting 4 μl of the lipid solution (pION CAT #110169) onto the filter plate (VWR CAT #13503). The membrane was then covered with 200 μl of acceptor well buffer at pH 7.4 (pION CAT #110139). The PAMPA assay plate (donor side and acceptor side) was combined and allowed to incubate at room temperature for 4 hours. The plate was then disassembled and spectrophotometer plates (VWR CAT #655801) were filled (150 μl/well). The donor, acceptor, reference, and blank plates were read in the SPECTRAMAX® UV plate reader. Data was captured by the pION software, which analyzes the spectra and generates Pc values.

hERG Patch Clamp

Whole-cell patch-clamp was used to directly measure hERG currents in HEK-293 cells stably expressing the cloned hERG potassium channel α subunit. The compound was tested in an aqueous buffer with pH 7.4 at room temperature. Repetitive test pulses (0.05 Hz) were applied from a holding potential of −80 mV to +20 mV for 2 seconds and tail currents were elicited following the test pulses by stepping the voltage to −65 mV. The effects from the compound were calculated by measuring inhibition of peak tail current Sodium Channel Patch Clamp Whole-cell patch-clamp was used to directly measure inward sodium currents in HEK-293 cells expressing the human cardiac sodium channel, SCN5A. The compound was tested at a protein-free aqueous buffer. For determining steady state inhibition, sodium currents were elicited every 5 seconds using the following voltage protocol: cells were held at a potential of −90 mV and stepped to −20 mV for 60 ms. Effects were calculated by measuring inhibition of peak current during the test pulse to −20 mV. Rate-dependence of inhibition was assessed by stimulation at frequencies of 1 Hz and 4 Hz.

Single-Dose Pharmacokinetics in Rats

Male Sprague-Dawley rats (250-300 g) were used for the pharmacokinetic studies. Rats were fasted overnight prior to PO dosing and fed 4 h post dose. Blood samples (~0.3 mL) were collected from the jugular vein into K$_2$EDTA-containing tubes and then centrifuged at 4° C. (1500-2000×g) to obtain plasma. In an oral bioavailability study, 2 groups of animals (N=2-3 per group) received the test compound either as an intravenous (IV) infusion (over 10 min) via the jugular vein or by oral gavage. Serial blood samples were obtained at 0.17 (for IV only), 0.25, 0.5, 0.75, 1, 2, 4, 6, 8, and 24 h post dose. Plasma samples, obtained by centrifugation at 4° C. (1500-2000×g), were stored at −20° C. until analysis by LC/MS/MS.

Single-Dose Pharmacokinetics in Monkeys

The pharmacokinetics of various test compounds were evaluated in male cynomolgus monkeys in a crossover-design. Monkeys were fasted overnight prior to PO dosing and fed 4 h post dose. A group of 1-3 animals (3 to 5 kg) received the compound by IV infusion (over 10 min) via a femoral vein and by oral gavage, with a 1-week washout between treatments. Serial blood samples (~0.3 mL) were collected from a femoral artery at 0.17 (IV only), 0.25, 0.5, 0.75, 1, 2, 4, 6, 8, and 24 h post dose, and centrifuged at 4° C. (1500-2000×g) to obtain plasma. Samples were stored at −20° C. until analysis by LC/MS/MS.

Data Analysis for Pharmacokinetic Assays

The pharmacokinetic parameters were obtained by non-compartmental analysis of plasma concentration vs. time data (Kinetica software, Version 4.2, InnaPhase Corporation, Philadelphia, Pa.). The peak concentration ($C_{max}$) and time for $C_{max}$ were recorded directly from experimental observations. The area under the curve from time zero to the last sampling time (AUC(0-T)) was calculated using a combination of linear and log trapezoidal summations. The total plasma clearance (CLTp), steady-state volume of distribution (Vss), apparent elimination half-life (T½) and mean residence time (MRT) were estimated after IV administration. Estimations of T½ was made using a minimum of 3 time points with quantifiable concentrations. The absolute oral bioavailability (F) was estimated as the ratio of dose-normalized AUC values following oral and IV doses.

CCR-2 Calcium Mobilization

Human CCR-2-mediated intracellular calcium flux assay was established with the human monocytic cell line THP-1 monocytic cell line. THP-1 cells were first loaded with fluorophore by resuspending them in a glucose- and HEPES-buffered PBS (pH 7.4) containing 4 μM fluo-3 (Molecular Probes) and 1.25 mM Probenecid and then incubated for 60 minutes at 37° C. After washing once to remove excess fluo-3, the cells were re-suspended in washing buffer (containing phenol red-free RPMI) with 1.25 mM Probenecid, and plated into 96-well plate at $2\times10^5$/well. The plate was placed in a FLIPR®-1 (Molecular Devices) that uses an argon-ion laser to excite the cells and robotically adds the test compound and human MCP-1 while monitoring changes in fluorescence. Test compound dilutions with a range of concentration from 0 to 100 nM or buffer alone were added to each well, centrifuged and incubated for 10 minutes. Recombinant human MCP-1 (PeproTech Inc.) was then added to a final concentration of 10 nM. The fluorescence shift was monitored and the base-to-peak excursion computed automatically. All conditions were tested in duplicate. The inhibition achieved by graded concentrations of compound was calculated as a percentage of the compound-free MCP-1 control.

CCR-5 Calcium Mobilization

A similar procedure to the CCR-2 calcium mobilization set forth above was adopted except that MIP-1β (50 nM) was the ligand and the cell line was HT1080/CCR-5 in which endogenous CCR-5 is upregulated by random activation of gene expression (RAGE) technology.

CCR-2 GTP-γS Exchange

The MCP-1 dependent binding of [$^{35}$S]-GTPγS to CCR-2 was determined using membranes prepared from the HT1080 human cell line in which endogenous CCR-2 was upregulated by RAGE technology (Athersys). Each reaction (200 μL) contained 20 mM Na-HEPES, 10 mM $MgCl_2$, 50 mM NaCl, 0.1% BSA (Sigma), 1% DMSO, and 10 μM GDP (pH 7.4). The EC50 for MCP-1 dependent binding of [$^{35}$S]-GTPγS was determined by varying the MCP-1 concentrations from 1 pM to 1 μM. Reactions were incubated for 90 minutes hour at room temperature and [$^{35}$S]-GTPγS/Gα$_i$ complexes were collected on a Millipore MAFC 96 well filter plate. The inhibition of MCP-1 dependent [$^{35}$S]-GTPγS binding to CCR-2 membranes by the test compound was determined at 1 nM MCP-1 under identical conditions. Data were analyzed using the ligand binding software from Graphpad Prism 4.

CCR-5 GTP-γS Exchange

A similar procedure to the CCR-2 GTP-γS exchange procedure set forth above was adopted except that MIP-1α/LD78β was the ligand and the cell line was CCR-5/HT1080. MIP-1α/LD78β was used as the CCR-5 ligand because it provided a bigger signal to noise ratio than MIP-1β.

CCR-2 Whole Blood Integrin (CD11b) Upregulation

A CCR-2-dependent CD11b upregulation assay was established with human whole blood. Whole blood (100 μl) was pre-incubated with a concentration range of Example 1 at 37° C. for 10 minutes. Human recombinant MCP-1 (10 μl of 100 nM) was then added to each reaction to a final concentration of 10 nM, except for unstimulated control reactions. The reactions were incubated for 30 minutes at 37° C. After incubation, 1 ml of ice cold FACS (PBS with 10% FBS) buffer was added, and the samples were centrifuged at 1500 rpm for 5 minutes and re-suspended in 50 μl of FACS buffer. The cells were then incubated with 20 μl of anti-CD14-FITC/anti-CD11b-PE solution for 20 minutes on ice in the dark followed by addition of 1 ml of 1×FACS lysing solution (Becton Dickinson) to each reaction. The samples were then incubated for 30 minutes on ice in the dark. Following fixation and red blood cell lysis, the cells were centrifuged and resuspended in 200 μl FACS-lysing solution. Samples were analyzed by flow cytometry within 1 hour of staining using a FACSCalibur flow cytometer. Data acquisition and analysis were performed using CellQuestPro software. A sequential gating strategy was used to analyze the $CD14^{high}$ $CD11b^+$ monocyte population. For analysis, CD11b was measured as median fluorescence intensity (MFI).

CCR-5 Whole Blood CD11b Upregulation

Similar procedure to the CCR-2 whole blood CD11b upregulation procedure set forth above was adopted except that MIP-1β (50 nM) was used as the ligand.

Find below data for compared compounds (See WO 2008/014381 A1, WO 2008/014360 A1 and WO 2008/014361 A1). The comparative data shows the unexpected combination of equipotent dual CCR-2 and CCR-5 receptor inhibitory and desirable pharmacological characteristics.

TABLE 2

Comparative In vitro Data

| Compound | CCR-2 Binding $IC_{50}$ (nM) | CCR-5 Binding $IC_{50}$ (nM) | hERG FLUX $IC_{50}$ (nM) | $Na^+$ channel binding (% inhibition) | PAMPA permeability (nm/sec) |
|---|---|---|---|---|---|
| Example 12as WO 2005/021500 | 0.27 (1) | Not available | 2,800 | Not available | Not available |
| Example 12aj WO 2005/021500 | 0.43 ± 0.06 (2) | Not available | 770 | Not available | Not available |
| Example 2k WO 2005/021500 | 0.7 ± 0.3 (23) | 2.3 ± 1.8 | 51,000 | 97%, 10,000 nM | 529 ± 157 (9) |
| Example 12bd WO 2005/021500 | 1.15 ± 0.07 (2) | Not available | >80,000 | 54%, 10,000 nM | 392 |
| Example 8a WO 2005/021500 | 1.83 ± 0.80 (12) | Not available | >80,000 | 3%, 10,000 nM 33%, 30,000 nM | 94 ± 58 (10) |
| Example 8e WO 2005/021500 | 2.20 ± 0.03 (2) | Not available | >80,000 | 6%, 10,000 nM | 2 ± 2 (2) |
| Example 9c WO 2005/021500 | 0.96 ± 0.26 (19) | Not available | >80,000 | 48%, 10,000 nM 75%, 30,000 nM | 145 ± 71 (8) |
| Example 1 WO 2008/014381 | 1.4 ± 0.5 (18) | 23.6 ± 12.0 | >80,000 | 0%, 10,000 nM; 21%, 30,000 nM | 443 ± 114 (8) |

TABLE 2-continued

Comparative In vitro Data

| Compound | CCR-2 Binding IC$_{50}$ (nM) | CCR-5 Binding IC$_{50}$ (nM) | hERG FLUX IC$_{50}$ (nM) | Na$^+$ channel binding (% inhibition) | PAMPA permeability (nm/sec) |
|---|---|---|---|---|---|
| Example 1 WO 2008/014360 | 2.74 ± 1.34 (15) | 6.3 ± 1.5 | >80,000 | 13%, 10,000 nM 32%, 30,000 nM | 560 ± 86 (5) |
| Example 1 Present Invention | 6.2 ± 2.7 | 3.6 ± 1.8 | >80,000 | 46%, 30,000 nM | 336 |

TABLE 3

Additional Comparative In vitro Data

| Compound | CCR-2 Chemotaxis IC$_{50}$ (nM) | CCR-5 Chemotaxis IC$_{50}$ (nM) | hERG patch clamp (% Inhib.) | Na$^+$ channel patch clamp (% Inhib.) |
|---|---|---|---|---|
| Example 2k U.S. Pat. No. 7,163,937 | 0.24 ± 0.16 (12) | Not available | 83%, 10,000 nM | 52%, 10,000 nM 90%, 30,000 nM |
| Example 8a WO 2005/021500 | 2.63 ± 1.24 (4) | Not available | 4%, 10,000 nM | 22%, 10,000 nM 49%, 30,000 nM |
| Example 9c WO 2005/021500 | 0.21 | Not available | 4%, 10,000 nM | 19%, 10,000 nM 39%, 30,000 nM |
| Example 1 WO 2008/014381 | 0.71 ± 0.16 (22) | Not available | 33%, 10,000 nM 61%, 30,000 nM | 17%, 10,000 nM 19%, 30,000 nM |
| Example 1 WO 2008/014360 | 0.8 ± 0.5 (16) | 1.1 ± 0.7 | 12%, 10,000 nM 19%, 30,000 nM | 29%, 30,000 nM |
| Example 1 Present Invention | 0.8 ± 0.8 | 1.1 ± 0.6 | 1.2%, 10,000 nM 9.2%, 30,000 nM | 15-20%, 10,000 nM 13-16%, 30,000 nM |

TABLE 4

Additional Comparative In vitro Data

| Compound | CCR-2 Ca$^{2+}$ Flux IC$_{50}$ (nM) | CCR-5 $^{2+}$ Flux IC$_{50}$ (nM) | CCR-2 GTP-γS IC$_{50}$ (nM) | CCR-5 GTP-γS IC$_{50}$ (nM) |
|---|---|---|---|---|
| Example 2k U.S. Pat. No. 7,163,937 | Not available | Not available | Not available | Not available |
| Example 1 WO 2008/014381 | 0.9 | 24.0 | 5 | 111.0 |
| Example 1 WO 2008/014360 | 0.8 ± 0.6 | 5.9 ± 3.3 | 3.5 ± 1.9 | 5.4 ± 3.2 |
| Example 1 Present Invention | 2.9 ± 1.5 | 2.0 ± 1.4 | 3.5 ± 1.9 | 6.1 ± 1.2 |

TABLE 5

Additional Comparative In vitro Data

| Compound | CCR-2 CD11b IC$_{50}$ (nM) | CCR-5 CD11b IC$_{50}$ (nM) |
|---|---|---|
| Example 2k U.S. Pat. No. 7,163,937 | 4.7 ± 0.9 | 4.3 ± 4.4 |
| Example 1 WO 2008/014381 | 0.77 ± 0.40 | Not available |
| Example 1 WO 2008/014360 | 2.6 ± 2.2 | 34.7 ± 11.0 |
| Example 1 Present Invention | 4.8 | 5.7 |

TABLE 6

Comparative In vivo Pharmacokinetic Data in the Rat

| Compound | Dose IV/PO (mg/kg) | Cl (mL/min/kg) | F % | Oral AUC (nM*h) |
|---|---|---|---|---|
| Example 2k WO 2005/021500 | 2.5/25 | 40 | 68 | 9294 |
| Example 8a WO 2005/021500 | 6/72 | 42 | 1.4 | 690 |
| Example 9c WO 2005/021500 | 4/43 | 54 | 14 | 1855 |
| Example 1 WO 2008/014381 | 2/10 | 43 | 51 | 3794 |
| Example 1 WO 2008/014360 | 2/10 | 25 | 79 | 10169 |
| Example 1 Present Invention | 2/10 | 49.7 | 94 | 6500 |

TABLE 7

Comparative In vivo Pharmacokinetic Data in the Monkey

| Compound | Dose IV/PO (mg/kg) | Cl (mL/min/kg) | F % | Oral AUC (nM*h) |
|---|---|---|---|---|
| Example 2k WO 2005/021500 | 1/1.4 | 25 | 46 | 862 |
| Example 8a WO 2005/021500 | 1/11 | 14 | 9.4 | 1896 |
| Example 9c WO 2005/021500 | 1/10 | 12 | 26 | 6763 |

TABLE 7-continued

Comparative In vivo Pharmacokinetic Data in the Monkey

| Compound | Dose IV/PO (mg/kg) | Cl (mL/min/kg) | F % | Oral AUC (nM*h) |
|---|---|---|---|---|
| Example 1 WO 2008/014381 | 1/1.3 | 23 | 47 | 836 |
| Example 1 WO 2008/014360 | 1/1 | 12 | 95 | 2352 |
| Example 1 Present Invention | 1/1 | 16.4 | 63 | 1300 |

Surprisingly, it was discovered that Example 1 of the present invention are not predominantly active against CCR-2 or CCR-5, but instead are equipotent dual antagonists, as measured by their CCR-2 and CCR-5 binding ability, and posses beneficial pharmacological characteristics. See Tables 2 to 5. For example, see Table 5 wherein Example 1 is equipotent against CCR-2 and CCR-5 while Examples 1 of WO 2008/014381 and WO 2008/014360 are predominantly active against CCR-2.

Utility

The compounds of the examples are shown to be modulators of chemokine receptor activity using assays know by those skilled in the art. In this section, we describe such assays and give their literature reference. More assays are described herein in the section titled "Comparative Pharmacological Characteristics", supra. By displaying activity in these assays of MCP-1 antagonism, compounds of the examples are expected to be useful in the treatment of human diseases associated with chemokines and their cognate receptors. The definition of activity in these assays is a compound demonstrating an $IC_{50}$ of 30 μM or lower in concentration when measured in a particular assay.

Antagonism of MCP-1-Induced Calcium Influx
(Sullivan et al., *Methods Mol. Biol.*, 114:125-133 (1999))

At least one compounds described in the examples have activity in the antagonism of MCP-1-induced calcium influx assay described here.

Calcium mobilization is measured using the fluorescent $Ca^{2+}$ indicator dye, Fluo-3. Cells are incubated at $8\times10^5$ cells/ml in phosphate-buffered saline containing 0.1% bovine serum albumin, 20 mM HEPES buffer, 5 mM glucose, 1% fetal bovine serum, 4 μM Fluo-3 AM and 2.5 mM Probenecid for 60 minutes at 37° C. Cells used for such calcium assays can include human monocytes isolated as described by Weiner et al., *J. Immunol. Methods*, 36:89-97 (1980) or cell lines which expresses the endogenous CCR-2 receptor such as THP-1 and MonoMac-6. The cells are then washed three times in phosphate-buffered saline containing 0.1% bovine serum albumin, 20 mM HEPES, 5 mM glucose and 2.5 mM Probenecid. The cells are resuspended in phosphate-buffered saline containing 0.5% bovine serum albumin, 20 mM HEPES and 2.5 mM Probenecid at a final concentration of $2-4\times10^6$ cells/ml. Cells are plated into 96-well, black-wall microplates (100 μl/well) and the plates centrifuged at 200×g for 5 minutes. Various concentrations of compound are added to the wells (50 μl/well) and after 5 minutes, 50 μl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Fluorometric Imaging Plate Reader (FLIPR®)-Based Functional Assay

HT1080 cells (clone 3559.1.6) were plated at 10,000 cells/well (30 microliters) in 384-well plates (black/clear bottom BIOCOAT® PDL, Beckton Dickinson) and charged with 30 microliters/well of Fluo-4 AM fluorescent dye (prepared by dissolving 1 mg Fluo-4 AM in 440 microliters DMSO and diluting with 100 microliters of pluronic solution before diluting further with 10 mL of Hanks buffer). The cells were incubated at 37° C. with 5% $CO_2$ for 30 min before being washed three times and suspended in Assay Buffer (20 mM HEPES, 1.2 mM $CaCl_2$, 5 mM $MgCl_2$, 2.5 mM Probenecid, 0.5% BSA, 1× Hanks). The test article was serially diluted in DMSO and then diluted 1:10 with Assay Buffer before being added to the cells (10 microliters/well). Using FLIPR®, the plates were read (10-70 sec) for induction of flux (i.e., agonist activity). The cells were then further charged with Agonist Solution (30 microliters/well; prepared by diluting 30 microliters of 100 microMolar MIP-1 beta in 100 mL of Assay Buffer; this protocol delivers a final concentration of 5 nM MIP-1 beta in the assay) and the plates were read using FLIPR® for one minute. Antagonist activity of the test article was determined relative to 0.4% DMSO/Buffer negative control.

In Vivo Assay(s) and Efficacy

N-((1R,2S,5R)-5-(tert-Butylamino)-2-((S)-3-(7-tert-butylpyrazolo[1,5-a][1,3,5]triazin-4-ylamino)-2-oxopyrrolidin-1-yl)cyclohexyl)acetamide (also referred to as "Example 1") was evaluated in the in vivo assay described below.

48-Hour Thioglycollate (TG)-Induced Peritonitis Model in hCCR-2 KI Mouse Methods The hCCR-2 KI mice (C57BL/6-SVJ129) were injected intraperitoneally with 1 ml of thioglycollate (TG) (Hardy Diagnostics). For each study, eight male mice per group were used. Example 1 was dosed orally 1 hour prior to TG injection. The vehicle used was 0.01 N HCl in water. Forty-eight hours post TG injection, peritoneal lavages were performed by injecting 5 ml PBS/10 mM EDTA/10% BSA into the peritoneal cavity.

For the 48-hour TG peritonitis study, Example 1 was dosed twice a day with the first dose one hour prior to TG injection. Total peritoneal cell counts were obtained on isolated cells by a cell counter. Cytospins were performed to determine differential leukocyte counts. The cells were stained for 3 minutes with Wright-Giemsa Stain (Sigma-Aldrich) and then rinsed with deionized water for 5 minutes. Differential counts were calculated based on a total of 200 cells counted per sample. Blood was also collected from the retro-orbital sinus at the end of each study in EDTA for determination of drug concentration.

For flow cytometric analysis, peritoneal exudate cells (1×10⁶) were washed once with FACS buffer (PBS/0.5% BSA) and resuspended in FACS buffer. Cells were incubated with an Fc-blocking antibody (BD Pharmingen) on ice for 15 min followed by addition of the following antibodies (BD Pharmingen): PE conjugated anti-F4/80, FITC conjugated anti-Ly6C, and Alexa 647 conjugated anti-hCCR-2. After 45 min on ice, cells were fixed by BD CYTOFIX® for 15 min on ice, washed twice with FACS buffer, and resuspended in 200 µl FACS buffer. Cellular events (40,000) were acquired for each sample and data were analyzed using FloJo software (TreeStar). A FSC/SSC gate was set to include all monocytes (low SSC, higher FSC) while excluding granulocytes from the analysis. This gated population was then analyzed for Ly6C (FITC), F4/80 (PE) expression. Peritoneal monocytes/macrophage numbers were determined by multiplying total peritoneal cell counts obtained by the cell counter and the percentage of monocytes/macrophages identified by F4/80⁺ cells from flow cytometry. Statistical significance of differences between means was analyzed using the paired two-tailed t test with significance set at p values below 0.05.

Results

Example 1 was evaluated in the hCCR-2 KI mouse TG peritonitis model to determine its EC50 in inhibiting monocyte/macrophage infiltration. Mice were administered thioglycollate, and dosed orally with Example 1 at 10, 50, or 160 mg/kg BID. Forty eight hours post TG treatment, peritoneal lavage was obtained for cellular infiltrate analysis by flow cytometry.

A dose-dependent inhibition in monocyte/macrophage infiltration was observed (FIG. 4). Doses of 10, 50, and 160 mg/kg gave an inhibition of 25%, 54% and 63%, respectively. Of the four separate studies with multiple doses, the maximal inhibition reached was ~70% and the average EC50 for inhibition of monocyte/macrophage infiltration by this analysis was estimated to be 4.9 nM, which correlates well with the in vitro IC50 (5.8±2.3 nM) for Example 1 inhibition of $^{125}$I-mouse MCP-1 binding to human CCR-2-expressing cells (hPBMCs).

To assess the in vivo level of receptor occupancy by Example 1 in the 48-hour thioglycolate peritonitis model in the hCCR-2 KI mouse, plasma levels of both Example 1 and mouse MCP-1 were measured. The caveat for this estimation is that only CCR-2 and its major ligand MCP-1 were taken into consideration. The receptor occupancy of a ligand in the presence of a competitive inhibitor is defined by the Gaddum equation:

$$\frac{[RL]}{[R]} = \frac{1}{1 + (K_d/[L])(1 + [I]/K_i)}$$

Since Example 1 is a competitive inhibitor of MCP-1 binding to CCR-2, the amounts of both mouse MCP-1/CCR-2 receptor complex and Example 1/CCR-2 receptor complex can be determined using the serum levels of both mouse MCP-1 and protein-unbound Example 1 in plasma. The $K_d$ for mouse MCP-1 binding to hCCR-2 is 0.91+/−0.08 nM (n=8) which was determined in cold competition ligand binding experiments using $^{125}$I-human MCP-1. The average $K_i$ for Example 1 binding to hCCR-2 is 2.0 nM. The fraction of mouse MCP-1/CCR-2 receptor complexes is determined using the form of the equation described above. To determine the fraction of Example 1/CCR-2 complexes the equation is re-defined as:

$$\frac{[RI]}{[R]} = \frac{1}{1 + (K_i/[I])(1 + [L]/K_d)}$$

Finally, the amount of CCR-2 free is determined from:

$$[CCR\text{-}2]_{total} = [CCR\text{-}2]_{free} + [\text{mouse MCP-1/CCR-2}] + [\text{Example 1/CCR-2}]$$

As shown in Table 8, the percent inhibition of monocyte/macrophage infiltration into the peritoneum at 48 hour reflects the percentage of Example 1/CCR-2 receptor complex.

TABLE 8

Determination of In vivo Receptor Occupancy of Example 1 in
Blood of hCCR-2 KI Mice in the 48-hour TG Peritonitis Model

| Dose mg/kg | Concentration of Mouse MCP-1 in plasma (nM) | Concentration of free Example 1 in plasma (nM) (fold IC90 CCR-2 binding) | % mouse MCP-1 bound CCR-2 | % Example 1 bound CCR-2 | % free CCR-2 | % inhibition of monocyte/ macrophage infiltration[a] |
|---|---|---|---|---|---|---|
| 200[a] | 0.068 | 136.4 | 0.11 | 98.45 | 1.44 | 71 |
| 160 | 0.046 | 62.0 | 0.16 | 96.72 | 3.12 | 63 |
| 50 | 0.048 | 16.6 | 0.56 | 88.74 | 10.69 | 54 |
| 10 | 0.021 | 1.9 | 1.17 | 48.15 | 50.68 | 25 |
| 0 | 0.022 | 0.0 | 2.36 | 0.00 | 97.64 | 0 |

[a]dose was selected from a different study from other doses in the table to provide an example of maximal inhibition. This dose provided a free plasma concentration of 1.9-fold IC90 the hCCR-2 KI binding.

Collectively, these results clearly demonstrate that Example 1 is a potent blocker of monocyte/macrophage infiltration with an EC50 of ~4.9 nM. Maximal inhibition of monocyte/macrophage infiltration by Example 1 can be achieved by 98.5% CCR-2 occupancy with this compound. Notably, the studies have demonstrated a similar reduction (~70-80%) in monocyte/macrophage infiltration in CCR-2-deficient mice.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjögren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, vasculitis, vulnerable plaques, venous neointimal hyperplasia reperfusion injury, dialysis-graft neointimal hyperplasia, artio-venous shunt intimal hyperplasia, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Compounds disclosed herein are useful to treat or prevent disorders selected from rheumatoid arthritis, osteoarthritis, septic shock, atherosclerosis, aneurism, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus, esophageal squamous cell carcinoma, neuropathic pain, and obesity.

In another aspect, the compounds are useful to treat or prevent inflammatory disorders selected from rheumatoid arthritis, osteoarthritis, atherosclerosis, aneurism, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

In another aspect, examples disclosed herein may be useful in for the treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burketts lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyosarcoma, and osteosarcoma; and other tumors including melanoma, xenoderma pigmentosum, keratoactanthoma, seminoma, thyroid follicular cancer, and teratocarcinoma.

In another embodiment, disclosed herein are methods of treating cancer, wherein the cancer is selected from breast cancer, liver cancer, prostate cancer, and melanoma. Additionally, compounds disclosed herein may be useful in the treatment of ovarian cancer, and multiple myeloma.

The present invention provides methods for the treatment of a variety of non-cancerous proliferative diseases.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds disclosed herein may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound is used contemporaneously with one or more other drugs, a pharmaceutical composition containing such other drugs in addition to the compound of the present invention may be used. Accordingly, the pharmaceutical compositions include those that also contain one or more other active ingredients, in addition to a compound of the present disclosure.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal antiinflammatory agents (NSAIDs)

such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-CoA reductase inhibitors (lovastatin, simvastatin, pravastatin, fluvastatin, atorvastatin, and other statins), sequestrants (cholestyramine and colestipol), nicotonic acid, fenofibric acid derivatives (gemfibrozil, clofibrat, fenofibrate and benzafibrate), and probucol; (k) antidiabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, compounds disclosed herein (or other formulae disclosed herein) may be administered in combination with other anti-cancer and cytotoxic agents and treatments useful in the treatment of cancer or other proliferative diseases. The invention herein further comprises use of the compounds herein (or other formulae disclosed herein), in preparing medicaments for the treatment of cancer, and/or it comprises the packaging of the compounds of herein together with instructions that the compounds be used in combination with other anti-cancer or cytotoxic agents and treatments for the treatment of cancer. The present invention further comprises combinations of the compounds of and one or more additional agents in kit form, e.g., where they are packaged together or placed in separate packages to be sold together as a kit, or where they are packaged to be formulated together.

The second (or more) anti-cancer agents may be selected from any one or more of the following:

alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors;

cell-cycle response modifiers; enzymes; farnesyl-protein transferase inhibitors;

hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors;

microtubule-disruptor agents, such as ecteinascidins or their analogs and derivatives; microtubule-stabilizing agents such as taxanes, and the naturally-occurring epothilones and their synthetic and semi-synthetic analogs;

microtubule-binding, destabilizing agents (including vinca alkaloids); and topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Additionally, the compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

The above other therapeutic agents, when employed in combination with the compounds of the present invention, can be used, for example, in those amounts indicated in the Physicians' Desk Reference (PDR) or as otherwise determined by one of ordinary skill in the art.

The compounds are administered to a mammal in a therapeutically effective amount. By "therapeutically effective amount" it is meant an amount of a compound of the present disclosure that, when administered alone or in combination with an additional therapeutic agent to a mammal, is effective to prevent or ameliorate the disease condition or the progression of the disease.

Dosage and Formulation

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily. In one embodiment, the daily oral dosage of the active ingredient is between 3 and 600 mg either administered once daily or in divided doses administered twice daily. Alternatively, the active ingredient may be administered in doses of 10-20 mg administered twice daily or 40 to 100 mg administered once daily. Alternatively, the active ingredient may be administered a dose of 12.5 mg twice a day or 75 mg once a day. Alternatively, the active ingredient may be administered in doses of 3, 10, 30, 100, 300, and 600 mg administered either once or twice a day.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

"Substantially pure" as used herein is intended to include a compound having a purity greater than about 90 weight percent, including about 90, 91, 92, 93, 94, 95, 96, 97, 98, 99, and 100 percent.

As one example, a compound disclosed herein may be substantially pure in having a purity greater than about 90 percent (by weight), where the remaining less than about 10 percent of material comprises other metabolite of the compound, a prodrug of the compound, and/or reaction and/or processing impurities arising from its preparation.

Obviously, numerous modifications and variations of the present invention are possible in light of the above teachings. It is therefore to be understood that within the scope of the appended claims, the invention may be practiced otherwise that as specifically described herein.

What is claimed is:

1. A method of treating a disorder, comprising administering to a patient in need thereof a therapeutically effective amount of a compound having the formula:

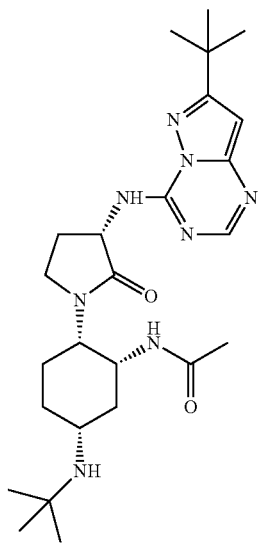 [SMILES: CC(=O)N[C@@H]1C[C@H](NC(C)(C)C)CC[C@@H]1N1CC[C@H](Nc2ncnc3cc(C(C)(C)C)nn23)C1=O]

or a salt thereof; wherein said disorder is selected from rheumatoid arthritis and breast cancer.

2. A method of treating a disorder, comprising administering to a patient in need thereof a therapeutically effective amount of a compound having the formula:
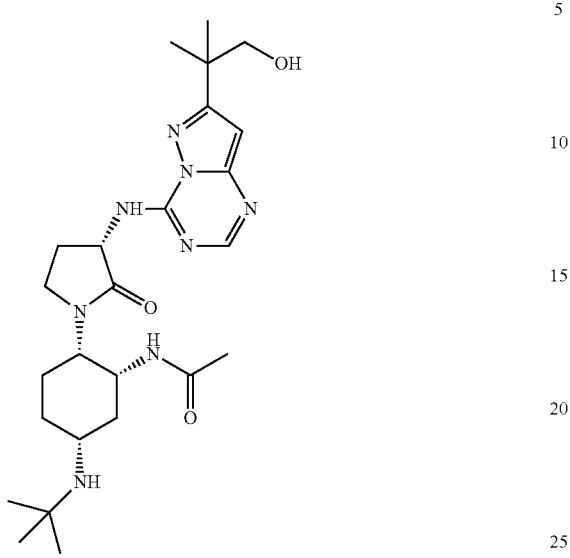
or a salt thereof; wherein said disorder is selected from rheumatoid arthritis and breast cancer.
* * * * *